US012012622B1

(12) United States Patent
Odaka et al.

(10) Patent No.: US 12,012,622 B1
(45) Date of Patent: Jun. 18, 2024

(54) ***PAENIBACILLUS PABULI*-DERIVED ENZYME CAPABLE OF PRODUCING GALACTO-OLIGOSACCHARIDE, AND METHOD FOR PRODUCING GALACTO-OLIGOSACCHARIDE**

(71) Applicant: GODO SHUSEI CO., LTD., Tokyo (JP)

(72) Inventors: Rei Odaka, Chiba (JP); Yasuhiro Baba, Chiba (JP); Junki Ogasawara, Chiba (JP); Jun Yoshikawa, Chiba (JP)

(73) Assignee: GODO SHUSEI CO., LTD., Tokyo (JP)

( * ) Notice: Subject to any disclaimer, the term of this patent is extended or adjusted under 35 U.S.C. 154(b) by 0 days.

(21) Appl. No.: 17/045,149

(22) PCT Filed: Mar. 28, 2019

(86) PCT No.: PCT/JP2019/013549
§ 371 (c)(1),
(2) Date: Oct. 2, 2020

(87) PCT Pub. No.: WO2019/194062
PCT Pub. Date: Oct. 10, 2019

(30) Foreign Application Priority Data

Apr. 5, 2018 (JP) .................................. 2018-073180
Apr. 5, 2018 (JP) .................................. 2018-073181

(51) Int. Cl.
*C12P 19/04* (2006.01)
*C12N 9/24* (2006.01)

(52) U.S. Cl.
CPC ............ *C12N 9/2402* (2013.01); *C12P 19/04* (2013.01); *C12Y 302/01108* (2013.01)

(58) Field of Classification Search
None
See application file for complete search history.

(56) References Cited

U.S. PATENT DOCUMENTS

| | | | |
|---|---|---|---|
| 5,032,509 A | 7/1991 | Matsumoto et al. | |
| 9,200,299 B2 * | 12/2015 | Friedman | C12N 9/16 |
| 10,676,751 B2 * | 6/2020 | Daniell | C12Y 302/01021 |
| 10,822,383 B2 * | 11/2020 | Cheng | C08B 37/0009 |
| 2011/0065152 A1 | 3/2011 | Avalakki et al. | |
| 2012/0129802 A1 | 5/2012 | Giacomelli et al. | |
| 2012/0135468 A1 | 5/2012 | Katase et al. | |
| 2016/0108447 A1 | 4/2016 | Giacomelli et al. | |
| 2017/0049120 A1 | 2/2017 | Katase et al. | |
| 2019/0136280 A1 | 5/2019 | Giacomelli et al. | |

FOREIGN PATENT DOCUMENTS

| | | |
|---|---|---|
| CN | 106957832 A | 7/2017 |
| JP | H05236981 A | 9/1993 |
| JP | 2652049 B2 | 9/1997 |
| JP | 2739335 B2 | 4/1998 |
| JP | 2011517553 A | 6/2011 |
| JP | 2013501504 A | 1/2013 |
| JP | 5643756 B2 | 12/2014 |

OTHER PUBLICATIONS

Z. Mozaffar et al., "Purification and Properties of b-Galactosidases from Bacillus circulans", Agric. Biol. Chem., 48, pp. 3053-3061 (1984) (9 pages).
H. Sotoya et al., "Identification of genes involved in galactooligosaccharide utilization in Bifidobacterium breve strain YIT 4014", Microbiology, 163, pp. 1420-1428 (2017) (9 pages).
S. S. van Leeuwen et al., "1H NMR analysis of the lactose/b-galactosidase-derived galacto-oligosaccharide components of Vivinal® GOS up to DP5", Carbohydrate Research, 400, pp. 59-73 (2014) (15 pages).
T. Moriya et al., "Synthesis of an allergy inducing tetrasaccharide "4P-X"", Carbohydrate Research, 439, pp. 44-49 (2017) (6 pages).
Y. Liu et al., "Biochemical characterization of a novel b-galactosidase from Paenibacillus barengoltzii suitable for lactose hydrolysis and galactooligosaccharides synthesis", International Journal of Biologicial Macromolecules, vol. 104, pp. 1055-1063 (2017) (9 pages).

(Continued)

*Primary Examiner* — Hope A Robinson
(74) *Attorney, Agent, or Firm* — Osha Bergman Watanabe & Burton LLP

(57) ABSTRACT

[Problem] To provide: a novel enzyme which is derived from a microorganism other than *Bacillus circulans* and is highly selective for galactotrisaccharide production and with which the galactooligosaccharide can be highly efficiently produced; and a novel method capable of producing the galactooligosaccharide. [Solution] A method for producing a galatooligosaccharide, the method including bringing an enzyme having an amino acid sequence selected from the group consisting of (a) to (f) and cells of a bacterium belonging to the genus *Paenibacillus* and/or a galactooligosaccharide-producing enzyme for the bacterium, into contact with lactose. (a) An amino acid sequence of sequence number 1. (b) An amino acid sequence of sequence number 2. (c) An amino acid sequence of an enzyme having galactooligosaccharide-producing activity, the amino acid sequence being the amino acid sequence of sequence number 1 in which one to ten amino acids have been replaced, removed, or inserted. (d) An amino acid sequence of an enzyme having galactooligosaccharide-producing activity, the amino acid sequence being the amino acid sequence of sequence number 2 in which one to ten amino acids have been replaced, removed, or inserted. (e) An amino acid sequence of an enzyme having galactooligosaccharide-producing activity, the amino acid sequence having a homology of 80% or higher but less than 100% to the amino acid sequence of sequence number 1. (f) An amino acid sequence of an enzyme having galactooligosaccharide-producing activity, the amino acid sequence having a homology of 80% or higher but less than 100% to the amino acid sequence of sequence number 2.

6 Claims, 3 Drawing Sheets

Specification includes a Sequence Listing.

(56) References Cited

OTHER PUBLICATIONS

E. Benesova et al., "b-D-Galactosidase from Paenibacillus thiaminolyticus catalyzing transfucosylation reactions" Glycobiology, vol. 20, pp. 442-451 (2010) (10 pages).

J. Lee et al., "*Paenibacillus woosongensis* sp. nov., a xylanolytic bacterium isolated from forest soil", International Journal of Systematic and Evolutionary Microbiology, vol. 58, pp. 612-616 (2008) (5 pages).

R. Rivas et al., "*Paenibacillus xylanilyticus* sp. nov., an airborne xylanolytic bacterium", International Journal of Systematic and Evolutionary Microbiology, vol. 55, pp. 405-408 (2005) (4 pages).

R. Ivy et al., "Identification and Characterization of Psychrotolerant Sporeformers Associated with Fluid Milk Production and Processing", Applied and Environmental Microbiology, vol. 78, pp. 1853-1864 (2012) (12 pages).

P. Isorna et al., "Crystal Structures of Paenibacillus polymyxa b-Glucosidase B Complexes Reveal the Molecular Basis of Substrate Specificity and Give New Insights into the Catalytic Machinery of Family I Glycosidases", J. Mol. Biol., vol. 371, pp. 1204-1218 (2007) (15 pages).

T. Sumida et al., "Utilization of Gaglioside-Degrading *Paenibacillus* sp. Strain TS12 for Production of Glucosylceramide", Applied and Environmental Microbiology, vol. 68, pp. 5241-5248 (2002) (8 pages).

International Preliminary Report on Patentability issued in International Application No. PCT/JP2019/013549, mailed Oct. 15, 2020 (9 pages).

International Search Report issued in International Application No. PCT/JP2019/013549, mailed May 7, 2019 (2 pages).

Abstract of Database UniProt [Online], "RecName: Full=Beta-galactosidase {ECO:0000256:ARBA:ARBA00013303, ECO: 0000256: RuleBase: RU361154}; EC=3.2.1.23 {ECO:0000256: ARBA: ARBA00012756, ECO: 0000256: RuleBase:RU361154}; AltName: Full=Lactase {ECO: 0000256:ARBA:ARBA00017614, ECO: 0000256:RuleBase: RU361154};" XP002804907; retrieved Apr. 29, 2015 (2 pages).

P.S. Panesar, et al., "Biocatalytic strategies in the production of galacto-oligosaccharides and its global status," International Journal of Biological Macromolecules, vol. 111, No. 12, pp. 667-679, XP055722031, Jan. 12, 2018 (13 pages).

Extended European Search Report issued in corresponding European Application No. 19782446.9; dated Jan. 10, 2022 (11 pages).

\* cited by examiner

[Fig. 1]
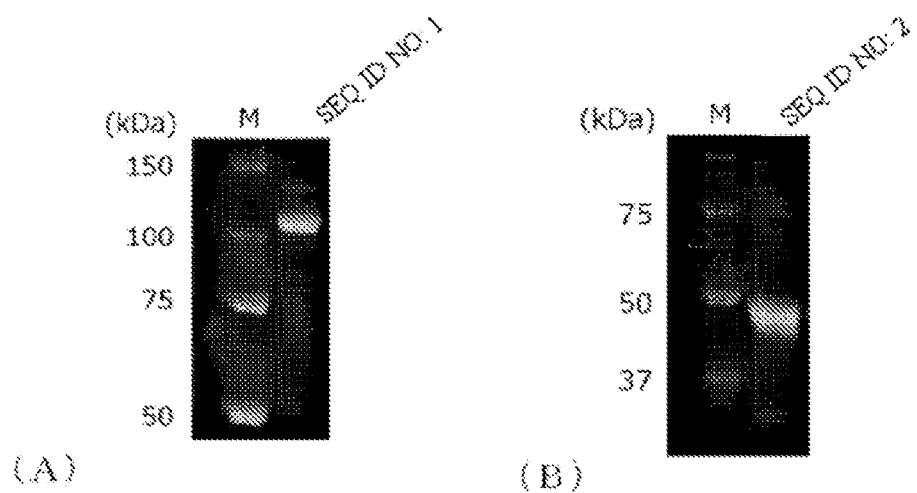
[Fig. 2]
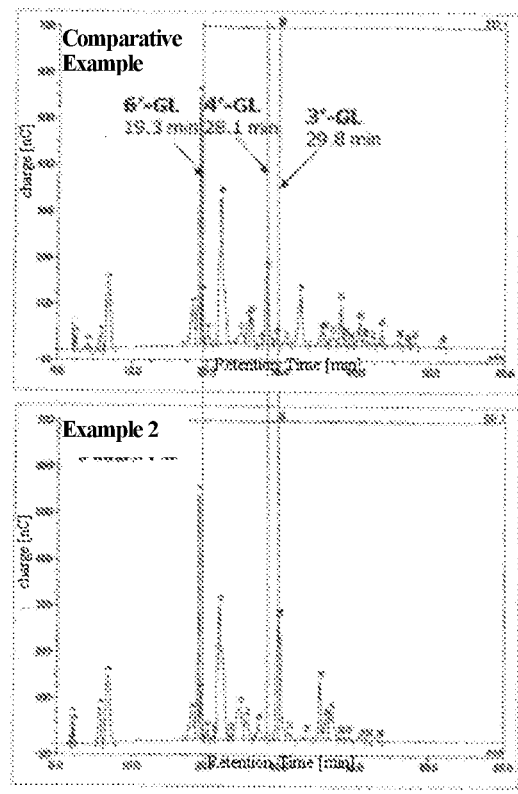

[Fig.3]
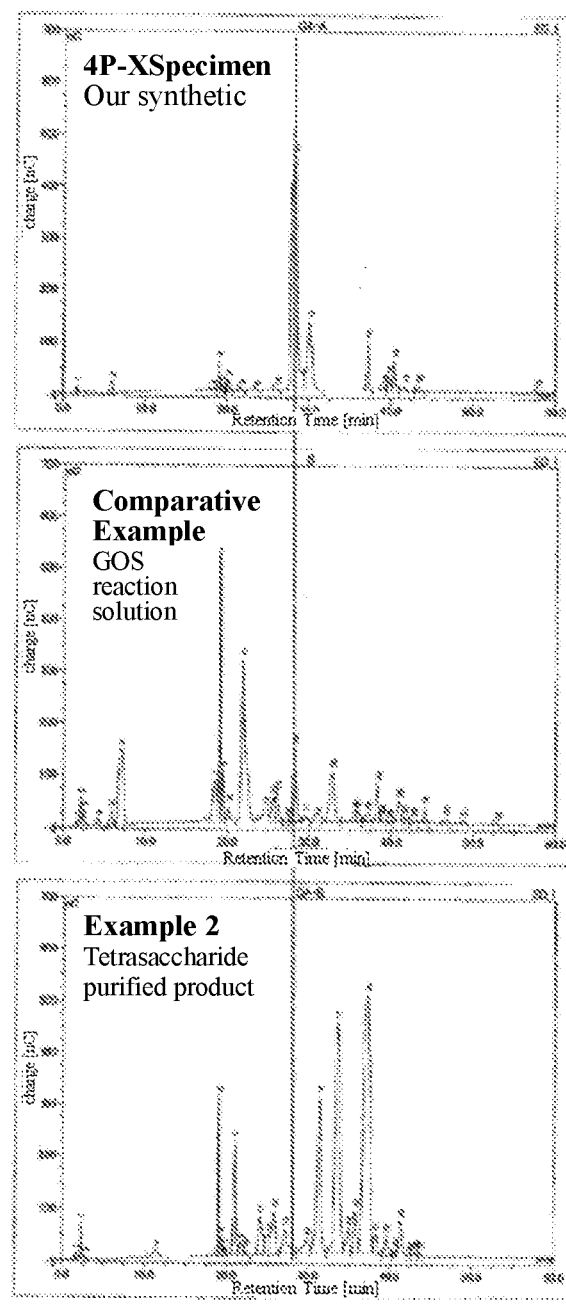

[Fig.4]
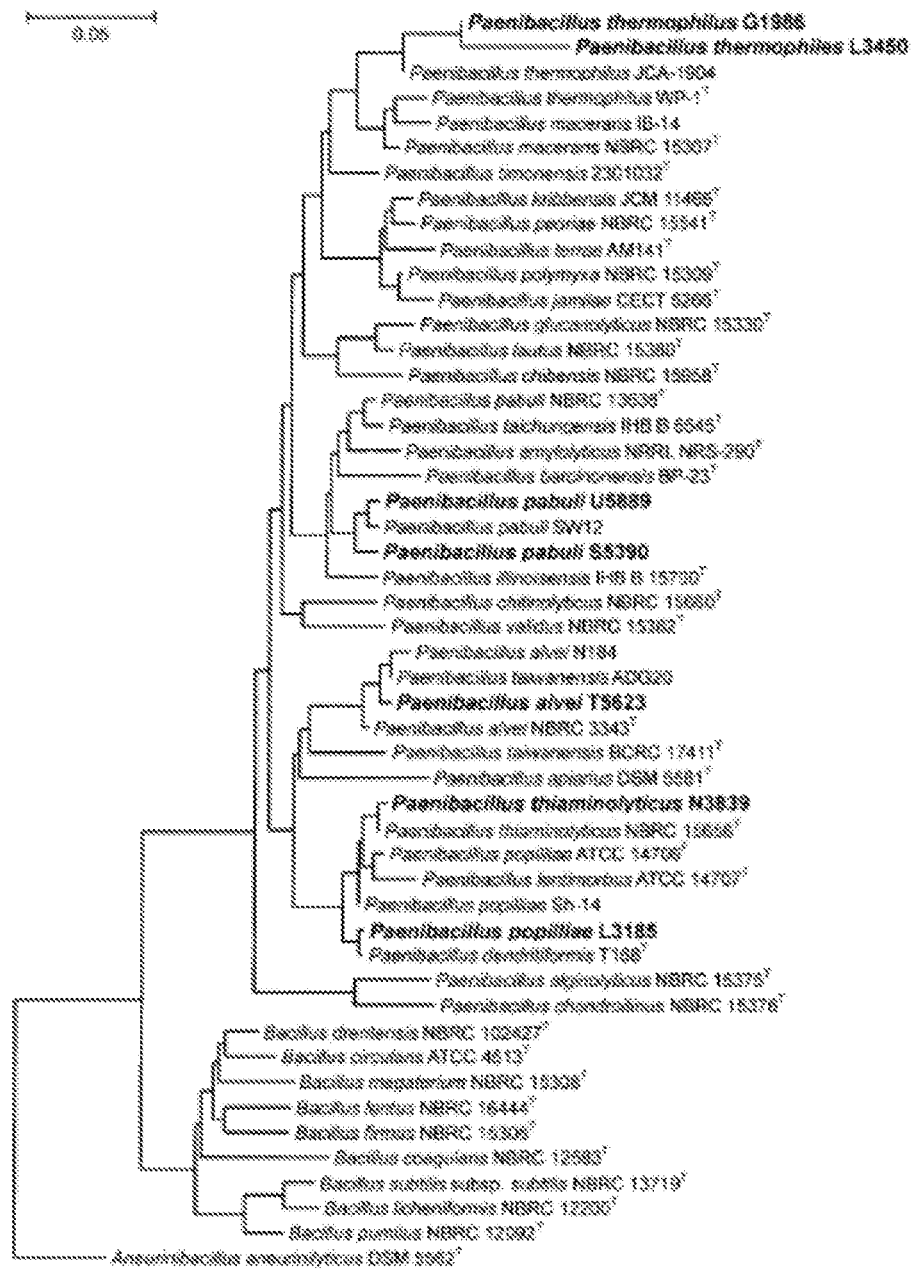

PAENIBACILLUS PABULI-DERIVED ENZYME CAPABLE OF PRODUCING GALACTO-OLIGOSACCHARIDE, AND METHOD FOR PRODUCING GALACTO-OLIGOSACCHARIDE

This application is a national stage entry of PCT/JP2019/013549 filed on Mar. 28, 2019, which claims priority to JP2018-073180 filed on Apr. 5, 2018, and JP2018-073181 filed on Apr. 5, 2018, the entire contents of these applications are incorporated herein by reference for all purposes.

TECHNICAL FIELD

The present invention relates to an enzyme capable of producing galacto-oligosaccharides. The present invention also relates to a DNA encoding the enzyme and a method for producing a galacto-oligosaccharide using the enzyme. The present invention also relates to a method for producing a galacto-oligosaccharide.

BACKGROUND ART

Galacto-oligosaccharides have been appreciated as the source of nutrition for useful bacteria, such as bifidobacteria living in the human intestinal bacterial flora. Therefore, various methods have been proposed as galacto-oligosaccharide production methods (e.g., Patent Literatures 1 to 6). The enzyme used therein is lactase, and the microorganisms used therein are lactase-producing microorganisms. Lactase (β-galactosidase) hydrolyzes lactose into β-galactose and glucose. Here, lactase can cause a reaction to transfer the β-galactosyl group resulting from the decomposition of lactose molecules into other lactose molecules or the like, and, as a result of the reaction, galacto-oligosaccharides can be produced.

CITATION LIST

Patent Literature

Patent Literature 1: Japanese Patent No. 2652049
Patent Literature 2: Japanese Patent No. 2739335
Patent Literature 3: Japanese Patent No. 5643756
Patent Literature 4: JP 5-236981 A
Patent Literature 5: Published Japanese Translation of PCT Patent Application No. 2011-517553
Patent Literature 6: Published Japanese Translation of PCT Patent Application No. 2013-501504

Non-Patent Literature

Non-Patent Literature 1: Z. Mozaffar, K. Nakanishi, R. Matsuno and T. Kamikubo, Purification and Properties of β-Galactosidases from *Bacillus circulans*, Agric. biol. chem., 48, 3053-3061 (1986)
Non-Patent Literature 2: Sotoya et al., Identification of genes involved in galacto-oligosaccharide utilization in *Bifidobacterium breve* strain YIT 4014T., Microbiology, 163, 1420-1428. (2017)
Non-Patent Literature 3: Van Leeuwen, S. S., 1H NMR analysis of the lactose/β-galactosidase-derived galacto-oligosaccharide components of Vivinal® GOS up to DPS., Carbohydrates. Res., 400, 59-73. (2014)
Non-Patent Literature 4: T. Moriya, N. Nagahata, R. Odaka, H. Nakamura, J. Yoshikawa, K. Kurashima, T. Saito, Synthesis of an allergy inducing tetrasaccharide "4P-X"., Carbohydrates. Res., 439, 44-49. (2017)

SUMMARY OF INVENTION

Technical Problem

Lactase commercially used for galacto-oligosaccharide production today is mainly derived from *Bacillus circulans*. Lactase derived from *Bacillus circulans* is advantageous in that the efficiency of galacto-oligosaccharide production is relatively high. However, a disadvantage exists in that this lactase is likely to produce tetra- or higher saccharide galacto-oligosaccharides. The yield of tetra- or higher saccharide galacto-oligosaccharides is lower than that of tri-saccharide galacto-oligosaccharides.

Against such a background, a first object of the present application is to provide an enzyme derived from microorganisms other than *Bacillus circulans*, having high production selectivity for trisaccharide galacto-oligosaccharides, and capable of producing galacto-oligosaccharides with high efficiency, and also a method for producing a galacto-oligosaccharide using the same.

In addition, as galacto-oligosaccharide production methods, there are a method using lactase-producing microorganisms and a method using lactase purified from such microorganisms. As compared with the case of using purified lactase, the production method using lactase-producing microorganisms is advantageous in that the step of enzyme purification can be omitted, and monosaccharides produced from a side reaction, such as glucose, are utilized by microorganisms and thus can be removed, for example. However, studies thereof are still insufficient.

Further, although *Bacillus* is well known as galacto-oligosaccharide-producing microorganisms, there are many *Bacillus* species known to be pathogenic, such as *Bacillus anthracis* and *Bacillus cereus*. Thus, safer galacto-oligosaccharide-producing bacteria have been demanded.

Against such a background, a second object of the present application is to identify microorganisms suitable for the production of galacto-oligosaccharides, and provide a method for producing a galacto-oligosaccharide using the microorganisms.

Solution to Problem

The present inventors have conducted extensive research on the first object described above, and, as a result, accomplished the present invention.

That is, the present invention 1 provides an enzyme having an amino acid sequence selected from the group consisting of the following (a) to (f):
  (a) an amino acid sequence set forth in SEQ ID NO: 1,
  (b) an amino acid sequence set forth in SEQ ID NO: 2,
  (c) an amino acid sequence of an enzyme having a galacto-oligosaccharide-producing activity, wherein the amino acid sequence is set forth in SEQ ID NO: 1 with one to ten amino acids being substituted, deleted, or inserted,
  (d) an amino acid sequence of an enzyme having a galacto-oligosaccharide-producing activity, wherein the amino acid sequence is set forth in SEQ ID NO: 2 with one to ten amino acids being substituted, deleted, or inserted,
  (e) an amino acid sequence of an enzyme having a galacto-oligosaccharide-producing activity, wherein the amino acid sequence has a homology of 80% or more and less than 100% to an amino acid sequence set forth in SEQ ID NO: 1, and
(f) an amino acid sequence of an enzyme having a galacto-oligosaccharide-producing activity, wherein the amino acid sequence has a homology of 80% or more and less than 100% to an amino acid sequence set forth in SEQ ID NO: 2.

In addition, the present invention also provides a DNA encoding the enzyme described above.

The present invention provides a DNA having a base sequence selected from the group consisting of the following (A) to (G):
(A) a base sequence set forth in SEQ ID NO: 5,
(B) a base sequence set forth in SEQ ID NO: 6,
(C) a base sequence encoding an enzyme having a galacto-oligosaccharide-producing activity, wherein the base sequence has a homology of 80% or more and less than 100% to a base sequence set forth in SEQ ID NO: 5,
(D) a base sequence encoding an enzyme having a galacto-oligosaccharide-producing activity, wherein the base sequence has a homology of 80% or more and less than 100% to a base sequence set forth in SEQ ID NO: 6,
(E) a base sequence encoding an enzyme having a galacto-oligosaccharide-producing activity, wherein the base sequence hybridizes with a base sequence complementary to a base sequence set forth in SEQ ID NO: 5 under stringent conditions,
(F) a base sequence encoding an enzyme having a galacto-oligosaccharide-producing activity, wherein the base sequence hybridizes with a base sequence complementary to a base sequence set forth in SEQ ID NO: 6 under stringent conditions, and
(G) a base sequence resulting from conservative base substitution of the base sequence of any one of the DNAs of (A) to (F).

Here, the stringent conditions may be conditions under which washing is performed at a salt concentration and a temperature corresponding to 60° C., 1×SSC, and 0.1% SDS.

In addition, the present invention also provides an enzyme encoded by the DNA described above and having a galacto-oligosaccharide-producing activity.

Further, the present invention provides a recombinant vector containing the DNA described above. A transformant having the DNA described above or this recombinant vector is also provided.

Further, the present invention provides a method for preparing an enzyme having a galacto-oligosaccharide-producing activity, including a step of culturing the transformant described above, and a step of recovering an enzyme having a galacto-oligosaccharide-producing activity from the cultured transformant.

Further, the present invention provides an enzyme-containing composition containing the enzyme described above as an active ingredient.

Further, the present invention provides a method for producing a galacto-oligosaccharide, including bringing lactose into contact with an enzyme having a galacto-oligosaccharide-producing activity produced by *Paenibacillus pabuli*.

Further, the present invention provides a method for producing a galacto-oligosaccharide, including bringing lactose into contact with the enzyme described above.

In addition, the present inventors have conducted extensive research on the second object described above. As a result, they have identified microorganisms heretofore unknown to produce galacto-oligosaccharides and further found that galacto-oligosaccharides are produced by the entire genus to which the microorganisms belong, and thus accomplished the present invention.

That is, the present invention 2 is a method for producing a galacto-oligosaccharide, including bringing cells of bacteria belonging to the genus *Paenibacillus* and/or a galacto-oligosaccharide-producing enzyme of the bacteria into contact with lactose.

The bacteria belonging to the genus *Paenibacillus* may be *Paenibacillus thermophilus*, *Paenibacillus popilliae*, *Paenibacillus thiaminolyticus*, *Paenibacillus pabuli*, *Paenibacillus alvei*, *Paenibacillus alginolyticus*, *Paenibacillus chibensis*, *Paenibacillus chitinolyticus*, *Paenibacillus chondroitinus*, *Paenibacillus glucanolyticus*, *Paenibacillus lautus*, *Paenibacillus macerans*, *Paenibacillus peoriae*, *Paenibacillus polymyxa*, *Paenibacillus validus*, *Paenibacillus apiarius*, *Paenibacillus jamilae*, *Paenibacillus kribbensis*, or *Paenibacillus terrae*.

The bacteria belonging to the genus *Paenibacillus* may be *Paenibacillus thermophilus*, *Paenibacillus popilliae*, *Paenibacillus thiaminolyticus*, *Paenibacillus pabuli*, *Paenibacillus alvei*, or *Paenibacillus polymyxa*.

Advantageous Effects of Invention

According to the present invention 1, it has become possible to produce a galacto-oligosaccharide with high efficiency and high production selectivity for trisaccharide galacto-oligosaccharides using a *Paenibacillus pabuli*-derived enzyme having a galacto-oligosaccharide-producing activity.

According to the present invention 2, it has become possible to provide a method for producing a galacto-oligosaccharide utilizing microorganisms capable of producing a galacto-oligosaccharide.

BRIEF DESCRIPTION OF DRAWINGS

FIG. 1 (A) The SDS-PAGE results of an enzyme consisting of an amino acid sequence set forth in SEQ ID NO: 1; the left lane is a marker. (B) The SDS-PAGE results of an enzyme consisting of an amino acid sequence set forth in SEQ ID NO: 2; the left lane is a marker.

FIG. 2 Charts showing the comparison between the GOS produced by the lactase of the comparative example and that by the lactase of Example 2.

FIG. 3 Charts showing the confirmation of the presence of allergenic tetrasaccharides in the GOS produced by the lactase of the comparative example and that by the lactase of Example 2.

FIG. 4 A simple molecular phylogenetic tree based on the 16S rDNA partial base sequences of the genus *Paenibacillus* and the genus *Bacillus*.

DESCRIPTION OF EMBODIMENTS

Present Invention 1

Hereinafter, the present invention 1 will be described.

In the present invention, "oligosaccharide" means a polysaccharide compound, ranging from trisaccharides to decasaccharides.

In the present invention, a galacto-oligosaccharide (also expressed as GOS) mainly means an oligosaccharide represented by the following general formula.

(Gal)n-Gal-Glc

Here, Gal represents a galactose residue, Glc represents a glucose residue, and n is an integer of 1 to 8, especially an integer of 1 to 3. The linkage pattern of each intersaccharide linkage is not particularly limited, but is typically a β-1,4-glycoside linkage. The intersaccharide linkage pattern (particularly Gal-Gal) may be also be a β-1,3-glycoside linkage.

Lactase is an enzyme that can hydrolyze lactose into β-galactose and glucose. Upon the decomposition, the β-galactosyl group can be transferred to another molecule. Transfer into water generates β-galactose, while transfer into lactose (Gal-Glc) generates a trisaccharide galacto-oligosaccharide (Gal-Gal-Glc) (n in the above formula is 1).

When such a transfer reaction of the β-galactosyl group takes place with a trisaccharide galacto-oligosaccharide (Gal-Gal-Glc) (n in the above formula is 1), a tetrasaccharide galacto-oligosaccharide ((Gal)2-Gal-Glc) (n in the above formula is 2) is generated. Similarly, when the reaction takes place with a tetrasaccharide galacto-oligosaccharide (n in the above formula is 2), a pentasaccharide galacto-oligosaccharide (n in the above formula is 3) is generated.

In the case where a trisaccharide galacto-oligosaccharide is produced, unimolecular glucose and a unimolecular trisaccharide galacto-oligosaccharide are generated from bimolecular lactose. The theoretical yield of the galacto-oligosaccharide at this time is about 74 mass %.

In the case where a tetrasaccharide galacto-oligosaccharide is produced, bimolecular glucose and a unimolecular tetrasaccharide galacto-oligosaccharide are generated from trimolecular lactose. The theoretical yield of the galacto-oligosaccharide at this time is about 65 mass %.

Therefore, in the case where galacto-oligosaccharides are produced from lactose, in terms of yield, it is most efficient to produce only trisaccharide galacto-oligosaccharides. Here, the yield of galacto-oligosaccharides (mass %) means the percentage obtained by dividing "galacto-oligosaccharide production" by "lactose consumption."

In the present invention, the lactase activity of an enzyme is defined by either of the following two methods.

An enzyme to be measured is added to a lactose solution (lactose concentration: 10%), and the glucose production under pH 6.5 and 40° C. conditions is measured and quantitatively determined. The enzyme activity that produces 1 μmol of glucose in 1 minute is defined as 1 LU.

An enzyme to be measured is added to an o-nitrophenyl-β-galactopyranoside (ONPG) solution (ONPG concentration: 1.65 mM), and the o-nitrophenyl production under pH 6.5 and 40° C. conditions is measured and quantitatively determined. The enzyme activity that produces 1 μmol of o-nitrophenyl in 1 minute is defined as 1 OU.

When the activity can be measured by at least one of these two methods, the enzyme may be judged as lactase. More specifically, when the activity is 0.2 LU/mL or more or 0.5 OU/mL or more, the enzyme may be judged as lactase.

However, even when an enzyme has a lactase activity, such an enzyme does not necessarily have a galacto-oligosaccharide-producing activity (also expressed as GOS-producing activity). The galacto-oligosaccharide-producing activity of an enzyme is evaluated by the method described below.

An enzyme to be measured is added to a lactose solution (lactose concentration: 60%) and settled or shaken under pH 6.5, 50° C. conditions for a predetermined period of time. In the case where the enzyme has a GOS-producing activity, GOS is produced from lactose during this period. After the elapse of a predetermined period of time, the reaction solution is analyzed by HPLC.

As the column used for HPLC, CARBOSep CHO-620 6.5ϕ×300 mm manufactured by Transgenomic, for example, can be mentioned. The analysis is performed under the following conditions: mobile phase: water, flow rate: 0.4 mL/min, temperature: 85° C., detection: RI.

When the proportion of the total HPLC peak area of GOS relative to the total peak area of monosaccharides, disaccharides, GOS (tri- or higher saccharides, mainly tri to pentasaccharides) is not lower than the reference value, the enzyme may be judged as having a galacto-oligosaccharide-producing activity. The reference value is usually 1%. As a matter of course, the higher the proportion, the higher the galacto-oligosaccharide-producing activity of the enzyme. In the case where an enzyme having a high galacto-oligosaccharide-producing activity is to be obtained, a high reference value may be set. Therefore, the reference value may also be set at 1%, 3%, 5%, 10%, 20%, 25%, 30%, 35%, or 40%.

(BgaD)

BgaD is lactase for GOS production that has been commercially most utilized and is *Bacillus circulans*-derived lactase. From the prior studies, it is known that BgaD is composed of four kinds of enzymes having different molecular weights, that is lactase having a molecular weight of 195 kDa (BgaD-A, SEQ ID NO: 3, GenBank code: BAJ61032), lactase having a molecular weight of 160 kDa (BgaD-B), lactase having a molecular weight of 135 kDa (BgaD-C), and lactase having a molecular weight of 86 kDa (BgaD-D, SEQ ID NO: 4) (Patent Literature 3). Among them, BgaD-D with the smallest size is known to have the highest GOS-producing activity, and is also abundantly present in the lactase preparation for GOS production "BIO-LACTA" commercially available from Amano Enzyme, Inc.

In the method for producing GOS of the present invention described below, the GOS yield in the case of using BgaD-D as lactase for GOS production is about 60 to 70%.

The GOS yield (%) is the percentage of GOS production/lactose consumption. GOS production and lactose consumption can be determined by HPLC analysis.

In the method for producing GOS of the present invention described below, the trisaccharide GOS production selectivity in the case of using BgaD-D as lactase for GOS production is about 60% at the maximum.

The trisaccharide GOS production selectivity (%) means the percentage of the production of trisaccharide GOS relative to the total production of GOS. The higher this value is, the more it is indicated that trisaccharide GOS is mainly produced. The total production of GOS and the production of trisaccharide GOS can be calculated by HPLC analysis. The trisaccharide GOS production selectivity is preferably 60% or more, more preferably 70% or more, still more preferably 75% or more, and particularly preferably 80% or more.

When BgaD-D is used to produce GOS, tetra- and higher saccharide GOS is also abundantly produced.

<Enzyme Having GOS-Producing Activity and DNA Encoding the Same>

According to a first mode of the present invention, a novel enzyme having a galacto-oligosaccharide-producing activity and a DNA encoding the enzyme are provided.

The present inventors have found an enzyme that has a low homology to BgaD, which is a *Bacillus circulans*-derived GOS-producing enzyme, and also has a high yield and high GOS production selectivity. Such enzymes include an enzyme consisting of an amino acid sequence set forth in SEQ ID NO: 1, an enzyme consisting of an amino acid sequence set forth in SEQ ID NO: 2, and homologues thereof.

The enzyme consisting of an amino acid sequence set forth in SEQ ID NO: 1 and the enzyme consisting of an amino acid sequence set forth in SEQ ID NO: 2 are each an enzyme produced by *Paenibacillus pabuli*. These amino acid sequences have both been identified and reported by the present inventors for the first time.

(Enzyme Consisting of Amino Acid Sequence Set Forth in SEQ ID NO: 1)

The molecular weight of the enzyme consisting of an amino acid sequence set forth in SEQ ID NO: 1 is about 114 kDa (see FIG. 1A). The homology thereof to BgaD-D is about 15%. It has turned out that this enzyme is an enzyme that functions as lactase and can be used for GOS production using lactose as a raw material.

In the method for producing GOS of the present invention described below, the GOS yield in the case of using the enzyme consisting of an amino acid sequence set forth in SEQ ID NO: 1 as lactase for GOS production is about 45 to about 60%. However, of the produced GOS, the trisaccharide GOS production selectivity is about 75% or more. Further, the Km value of this enzyme, which indicates the enzyme performance, is more excellent than that of BgaD-D.

(Enzyme Consisting of Amino Acid Sequence Set Forth in SEQ ID NO: 2)

The molecular weight of the enzyme consisting of an amino acid sequence set forth in SEQ ID NO: 2 is about 50 kDa (see FIG. 1B). The homology thereof to BgaD-D is about 8%. It has turned out that this enzyme is an enzyme that functions as lactase and can be used for GOS production using lactose as a raw material.

In the method for producing GOS of the present invention described below, the GOS yield in the case of using the enzyme consisting of an amino acid sequence set forth in SEQ ID NO: 2 as lactase for GOS production is about 60 to about 70%. In addition, of the produced GOS, the trisaccharide GOS production selectivity is about 80% or more.

The enzyme consisting of an amino acid sequence set forth in SEQ ID NO: 2 forms a β-1,3-glycoside linkage and, like this, highly selectively transfers a β-galactosyl group (β-galactose residue) into a saccharide (e.g., lactose). That is, the GOS produced by the enzyme consisting of an amino acid sequence set forth in SEQ ID NO: 2 is mostly trisaccharide GOS in which β-galactosyl groups are β-1,3-glycoside linked. Of ordinary intestinal bacteria, only bifidobacteria can decompose a β-1,3-glycoside linkage. Therefore, in the case where GOS rich in such saccharides is ingested, it is expected that bifidobacteria can preferentially utilize the GOS and thus grow in the intestines. Incidentally, in most of the conventional GOS, galactosyl groups are linked to lactose forming a β-1,4-glycoside linkage or β-1,6-glycoside linkage.

Like this, according to the enzyme consisting of an amino acid sequence set forth in SEQ ID NO: 1 and the enzyme consisting of an amino acid sequence set forth in SEQ ID NO: 2, while achieving a high GOS yield, high enzyme-chemical properties and high trisaccharide GOS selectivity are also simultaneously achieved. As a result of using these enzymes derived from *Paenibacillus pabuli*, the generation of tetra- or higher saccharide GOS, which causes a decrease in yield, can be reduced than before.

As a matter of course, it is inferred that a family enzyme of the enzyme consisting of an amino acid sequence set forth in SEQ ID NO: 1 and a family enzyme of the enzyme consisting of an amino acid sequence set forth in SEQ ID NO: 2 also produce similar effects.

Incidentally, as a matter of course, unless its function is impaired, the enzyme may have an additional region. As such additional regions, for example, regions such as tag domains can be mentioned. The position where such a region is added may be the N-terminal, the C-terminal, or both of them.

Therefore, as the first mode of the present invention, the following enzymes (1) to (5) are provided.

(1) An enzyme consisting of an amino acid sequence set forth in SEQ ID NO: 1.

(2) An enzyme consisting of an amino acid sequence set forth in SEQ ID NO: 2.

(3) A family enzyme (or a homologue) of an enzyme consisting of an amino acid sequence set forth in SEQ ID NO: 1.

(4) A family enzyme (or a homologue) of an enzyme consisting of an amino acid sequence set forth in SEQ ID NO: 2.

(5) An enzyme having a galacto-oligosaccharide-producing activity, wherein the enzyme is the enzyme of (1) to (4) with a peptide or the like added thereto.

When a certain enzyme E1 is a family (or a homologue) of another enzyme E2, this means that the homology (or may also be expressed as identity or similarity) of E1 and E2 based on the amino acid sequence is 80% or more, 85% or more, 90% or more, 91% or more, 92% or more, 93% or more, 94% or more, 95% or more, 96% or more, 97% or more, 98% or more, or 99% or more. The upper limit is not particularly set but is less than 100%. That is, the substitution, deletion, or insertion of at least one amino acid residue is present. The amino acid sequence homology can be easily calculated using a known software with the BLAST algorithm and the BLAST2.0 algorithm, for example.

When a certain enzyme E1 is a family (or homologue) of another enzyme E2, this means that, in particular, the amino acid sequence of the enzyme E1 can be achieved by the amino acid sequence of the enzyme E2 with one or more and ten or less amino acids being substituted, deleted, or inserted. Substitution means that an amino acid at a specific site is replaced with another amino acid. Deletion means that an amino acid at a specific site is deleted. Insertion means that an amino acid that has been absent is added to the inside of the amino acid sequence.

In addition to this, when a certain enzyme E1 and another enzyme E2 are a family (or homologue), this means that the enzyme E1 and the enzyme E2 can exhibit the same function. The activity ratio in the function is not particularly limited. For example, when an enzyme having a higher activity is defined as E1, and its activity is taken as 100%, the activity of the enzyme E2 having a lower activity is 1% or more, 5% or more, 10% or more, 20% or more, 30% or more, 40% or more, 50% or more, 60% or more, 70% or more, 80% or more, or 90% or more.

A family enzyme of the enzyme consisting of an amino acid sequence set forth in SEQ ID NO: 1 means an enzyme having a homology of 80% or more and less than 100% to the amino acid sequence set forth in SEQ ID NO: 1 and also having a galacto-oligosaccharide-producing activity. It particularly means an enzyme consisting of an amino acid sequence set forth in SEQ ID NO: 1 with one to ten amino acids being substituted, deleted, or inserted, and having a galacto-oligosaccharide-producing activity, In a family enzyme of the enzyme consisting of an amino acid sequence set forth in SEQ ID NO: 1, the lower limit of the homology to the amino acid sequence set forth in SEQ ID NO: 1 may be 85% or more, 90% or more, 91% or more, 92% or more, 93% or more, 94% or more, 95% or more, 96% or more, 97% or more, 98% or more, or 99% or more. Also in the case where the lower limit of the homology is any of them, the upper limit is less than 100%.

Similarly, a family enzyme of the enzyme consisting of an amino acid sequence set forth in SEQ ID NO: 2 means an enzyme having a homology of 80% or more and less than 100% to the amino acid sequence set forth in SEQ ID NO: 2 and also having a galacto-oligosaccharide-producing activity. It particularly means an enzyme consisting of an amino acid sequence set forth in SEQ ID NO: 2 with one to ten amino acids being substituted, deleted, or inserted, and having a galacto-oligosaccharide-producing activity, In a family enzyme of the enzyme consisting of an amino acid sequence set forth in SEQ ID NO: 2, the lower limit of the homology to the amino acid sequence set forth in SEQ ID NO: 2 may be 85% or more, 90% or more, 91% or more, 92% or more, 93% or more, 94% or more, 95% or more, 96% or more, 97% or more, 98% or more, or 99% or more. Also in the case where the lower limit of the homology is any of them, the upper limit is less than 100%.

Therefore, more specifically, as the first mode of the present invention, the following enzymes (1) to (7) are provided.

(1) An enzyme consisting of an amino acid sequence set forth in SEQ ID NO: 1.

(2) An enzyme consisting of an amino acid sequence set forth in SEQ ID NO: 2.

(3) An enzyme consisting of an amino acid sequence set forth in SEQ ID NO: 1 with one to ten amino acids being substituted, deleted, or inserted, wherein the enzyme has a galacto-oligosaccharide-producing activity.

(4) An enzyme consisting of an amino acid sequence set forth in SEQ ID NO: 2 with one to ten amino acids being substituted, deleted, or inserted, wherein the enzyme has a galacto-oligosaccharide-producing activity.

(5) An enzyme having a galacto-oligosaccharide-producing activity, wherein the enzyme consists of an amino acid sequence having a homology of 80% or more and less than 100% to an amino acid sequence set forth in SEQ ID NO: 1.

(6) An enzyme having a galacto-oligosaccharide-producing activity, wherein the enzyme consists of an amino acid sequence having a homology of 80% or more and less than 100% to an amino acid sequence set forth in SEQ ID NO: 2.

(7) An enzyme having a galacto-oligosaccharide-producing activity, wherein the enzyme is the enzyme of (1) to (6) with a peptide or the like added thereto.

In other words, as the first mode of the present invention, enzymes having the following amino acid sequences (a) to (f) or consisting of the amino acid sequences (a) to (1) are provided.

(a) An amino acid sequence set forth in SEQ ID NO: 1.

(b) An amino acid sequence set forth in SEQ ID NO: 2.

(c) An amino acid sequence of an enzyme having a galacto-oligosaccharide-producing activity, wherein the amino acid sequence is set forth in SEQ ID NO: 1 with one to ten amino acids being substituted, deleted, or inserted.

(d) An amino acid sequence of an enzyme having a galacto-oligosaccharide-producing activity, wherein the amino acid sequence is set forth in SEQ ID NO: 2 with one to ten amino acids being substituted, deleted, or inserted.

(e) An amino acid sequence of an enzyme having a galacto-oligosaccharide-producing activity, wherein the amino acid sequence has a homology of 80% or more and less than 100% to an amino acid sequence set forth in SEQ ID NO: 1.

(f) An amino acid sequence of an enzyme having a galacto-oligosaccharide-producing activity, wherein the amino acid sequence has a homology of 80% or more and less than 100% to the amino acid sequence set forth in SEQ ID NO: 2.

In addition, the first mode of the present invention also provides a DNA encoding the enzyme described above. As long as the enzyme described above is encoded, DNAs consisting of any base sequences are within the scope of the present invention. In particular, DNAs consisting of the base sequences described below in detail are typical examples of such DNAs.

A DNA consisting of a base sequence set forth in SEQ ID NO: 5 encodes the enzyme consisting of an amino acid sequence set forth in SEQ ID NO: 1 (including the stop codon at the 3'-terminal). A DNA consisting of a base sequence set forth in SEQ ID NO: 6 encodes the enzyme consisting of an amino acid sequence set forth in SEQ ID NO: 2 (including the stop codon at the 3'-terminal). As described above, enzymes consisting of amino acid sequences set forth in SEQ ID NO: 1 and SEQ ID NO: 2 each have an excellent galacto-oligosaccharide-producing activity. Therefore, enzymes encoded by DNAs consisting of base sequences having a high homology to these base sequences are highly likely to be enzymes having a galacto-oligosaccharide-producing activity.

In addition, a DNA consisting of a base sequence resulting from conservative base substitution of the above DNA is also encompassed by the present invention. Conservative base substitution of a base sequence means, of base substitutions in a base sequence, a substitution that does not cause a change in the amino acid sequence of the enzyme to be encoded. That is, it means that two or more DNAs are in such a relation that they have base sequences different from each other but encode the enzyme of the same amino acid sequence.

Incidentally, as a matter of course, unless the function of itself or the encoded enzyme is impaired, the DNA may have an additional region. As such additional regions, for example, the repeating structure of the DNA itself, the stop codon or operator sequences, regions corresponding to the tag peptides, and the like can be mentioned. The position where such a region is added may be the 5'-terminal, the 3'-terminal, or both of them.

Therefore, as the first mode of the present invention, the following DNAs (1) to (6) are provided.

(1) A DNA consisting of a base sequence set forth in SEQ ID NO: 5.

(2) A DNA consisting of a base sequence set forth in SEQ ID NO: 6.

(3) A DNA encoding an enzyme having a galacto-oligosaccharide-producing activity, wherein the DNA consists of a base sequence having a high homology to a base sequence set forth in SEQ ID NO: 5.

(4) A DNA encoding an enzyme having a galacto-oligosaccharide-producing activity, wherein the DNA consists of a base sequence having a high homology to a base sequence set forth in SEQ ID NO: 6.

(5) A DNA consisting of a base sequence resulting from conservative base substitution of any one of the DNAs of (1) to (4).

(6) A DNA encoding an enzyme having a galacto-oligosaccharide-producing activity, wherein the DNA is the DNAs of (1) to (5) with the DNAs of (1) to (5), a stop codon or operator sequence, or the like added thereto.

A DNA consisting of a base sequence having a high homology (or may also be expressed as identity or similarity) to the base sequence of a certain DNA means a DNA consisting of a base sequence whose homology to the base sequence of the certain DNA is 80% or more, 85% or more, 90% or more, 91% or more, 92% or more, 93% or more, 94% or more, 95% or more, 96% or more, 97% or more, 98% or more, or 99% or more. The upper limit is not particularly set and is less than 100%. The DNA base sequence homology can be easily calculated using a known software with the BLAST algorithm and the BLAST2.0 algorithm, for example.

Separately therefrom/in addition thereto, a DNA consisting of a base sequence having a high homology to the base sequence of a certain DNA means a DNA that hybridizes or can hybridize with a DNA consisting of a base sequence complementary to the base sequence of the certain DNA under stringent conditions.

Here, "stringent conditions" means conditions under which a so-called specific hybrid is formed, and a non-specific hybrid is not formed. The stringency of hybridization is mainly determined by the conditions of the temperature, the ionic strength, and the denaturant. As the stringent conditions, for example, conditions under which washing is performed at a salt concentration and a temperature corresponding to 60° C., 1×SSC, and 0.1% SDS can be mentioned. The conditions may also be conditions under which washing performed at a salt concentration and a temperature corresponding to 60° C., 0.1×SSC, and 0.1% SDS or conditions under which washing performed at a salt concentration and a temperature corresponding to 68° C., 0.1×SSC, and 0.1% SDS.

Therefore, more specifically, as the first mode of the present invention, the following DNAs (1) to (8) are provided.

(1) A DNA consisting of a base sequence set forth in SEQ ID NO: 5.

(2) A DNA consisting of a base sequence set forth in SEQ ID NO: 6.

(3) A DNA encoding an enzyme having a galacto-oligosaccharide-producing activity, wherein the DNA consists of a base sequence having a homology of 80% or more and less than 100% to a base sequence set forth in SEQ ID NO: 5.

(4) A DNA encoding an enzyme having a galacto-oligosaccharide-producing activity, wherein the DNA consists of a base sequence having a homology of 80% or more and less than 100% to a base sequence set forth in SEQ ID NO: 6.

(5) A DNA encoding an enzyme having a galacto-oligosaccharide-producing activity, wherein the DNA consists of a base sequence that hybridizes with a base sequence complementary to a base sequence set forth in SEQ ID NO: 5 under stringent conditions.

(6) A DNA encoding an enzyme having a galacto-oligosaccharide-producing activity, wherein the DNA consists of a base sequence that hybridizes with a base sequence complementary to a base sequence set forth in SEQ ID NO: 6 under stringent conditions.

(7) A DNA consisting of a base sequence resulting from conservative base substitution of any one of the DNAs of (1) to (6).

(8) A DNA encoding an enzyme having a galacto-oligosaccharide-producing activity, wherein the DNA is the DNAs of (1) to (7) with the repeating structures of the DNAs of (1) to (7), a stop codon or operator sequence, or the like added thereto.

In other words, as the first mode of the present invention, DNAs having the following base sequences (A) to (G) or consisting of the base sequences (A) to (G) are provided.

(A) A base sequence set forth in SEQ ID NO: 5.

(B) A base sequence set forth in SEQ ID NO: 6.

(C) A base sequence encoding an enzyme having a galacto-oligosaccharide-producing activity, wherein the base sequence has a homology of 80% or more and less than 100% to a base sequence set forth in SEQ ID NO: 5.

(D) A base sequence encoding an enzyme having a galacto-oligosaccharide-producing activity, wherein the base sequence has a homology of 80% or more and less than 100% to a base sequence set forth in SEQ ID NO: 6.

(E) A base sequence encoding an enzyme having a galacto-oligosaccharide-producing activity, wherein the base sequence hybridizes with a base sequence complementary to a base sequence set forth in SEQ ID NO: 5 under stringent conditions.

(F) A base sequence encoding an enzyme having a galacto-oligosaccharide-producing activity, wherein the base sequence hybridizes with a base sequence complementary to a base sequence set forth in SEQ ID NO: 6 under stringent conditions.

(G) A base sequence resulting from conservative base substitution of any one of the base sequences of (A) to (F).

Incidentally, DNAs as described above can be obtained, for example, by collecting a genomic DNA from bacteria of the genus *Paenibacillus* (particularly *Paenibacillus pabuli*), followed by PCR using the same as the template.

As a pair of primers for amplifying the structural gene encoding the enzyme consisting of an amino acid sequence set forth in SEQ ID NO: 1 or its homologue, for example, primers 1 and 2 can be mentioned.

```
Primer 1:
5'-GAACACAAGGTCATGAAAGCAGCAAAGGCAGAT-3'

Primer 2:
5'-CATCCTGTTAAGCTTTTACAATGCCCGAATGAC-3'
```

As a pair of primers for amplifying the structural gene encoding the enzyme consisting of an amino acid sequence set forth in SEQ ID NO: 2 or its homologue, for example, primers 3 and 4 can be mentioned.

```
Primer 3:
5'-GAACACAAGGTCATGACCATTTTTCAATTTCCG-3'

Primer 4:
5'-CATCCTGTTAAGCTTTTAACGGATTTCCAGCCAATTG-3'
```

In this manner, the structural gene encoding the enzyme consisting of an amino acid sequence set forth in SEQ ID NO: 1 or its homologue (e.g., a DNA consisting of a base sequence set forth in SEQ ID NO: 5) or a structural gene encoding the enzyme consisting of an amino acid sequence set forth in SEQ ID NO: 2 or its homologue (e.g., DNA consisting of a base sequence set forth in SEQ ID NO: 6) can be acquired.

<Vector>

As a second mode of the present invention, a recombinant vector containing the DNA of the first mode is provided. This recombinant vector allows for the preparation of a transformant and the mass expression of an enzyme.

The vector is not particularly limited, and commonly used ones can be used. For example, plasmids, phages, cosmids, phagemids, and the like can be mentioned.

As plasmids, for example, pK4, pRK401, pRF31, pBR322, pBR325, pUC118, pUC119, pUC18, pBIC, pUB110, pTP5, YEp13, YEp24, YCp50, and the like can be mentioned.

As phages, λ phages (λgt10, λgt11, λZAP, etc.) can be mentioned. Further, it is also possible to use animal viruses, such as retrovirus or vaccinia virus, and insect viral vectors, such as baculovirus.

The vector may have connected thereto a cis-element such as a promoter or an enhancer, a splicing signal, a poly-A addition signal, a selective marker, a ribosome-binding sequence (SD sequence), a start codon, a stop codon, or the like. In addition, a tag sequence for facilitating the purification of the enzyme to be produced may also be connected. As tags, known tags such as His tags, GST tags, and MBP tags can be utilized. In addition, the vector may also contain an antibiotic resistance gene for selection, for example.

The technique for inserting a DNA into the vector is not particularly limited, and commonly used ones can be used. Usually, insertion is performed by the following technique. First, a purified DNA is cleaved with a suitable restriction enzyme, inserted into the restriction enzyme site or the multi-cloning site of the vector DNA, and thus connected to the vector.

<Transformant>

According to a third mode of the present invention, a transformant containing (or having introduced thereinto) the DNA of the first mode and/or the recombinant vector of the second mode is provided.

The organism to serve as a host for the transformant is not particularly limited, and commonly used ones can be used. Prokaryotic organisms, archaebacteria, and eukaryotic organisms are all usable, examples thereof including true bacteria (*E. coli*, etc.), yeast, plant cells, animal cells (COS cells, CHO cells, etc.), and insect cells.

As hosts, in particular, microorganisms of the genus *Bacillus*, the genus *Paenibacillus*, the genus *Brevibacillus* (e.g., *Brevibacillus chosinensis*), the genus *Escherichia* (e.g., *Escherichia coli*), the genus *Corynebacterium*, the genus *Saccharomyces*, the genus *Shizosaccharomyces*, the genus *Kluyveromyces*, the genus *Pichia*, the genus *Aspergillus*, the genus *Penicillium*, and the genus *Trichoderma* can be mentioned. In addition, microorganisms with meal experiences, such as lactic acid bacteria and acetic acid bacteria, can be mentioned.

The technique for introducing a DNA and/or a recombinant vector into these hosts is not particularly limited. For example, an electroporation method, a spheroplast method, a lithium acetate method, a calcium phosphate method, a lipofection method, and the like can be mentioned. It is also possible to utilize homologous recombination or the like to perform insertion or addition into the host's genome.

Incidentally, as a technique for checking whether the DNA or the recombinant vector has been introduced into the host, an arbitrary technique can be used. For example, a PCR method, a Southern hybridization method, a Northern hybridization method, and the like are applicable.

Utilizing the transformant described above, by a conventionally known method, the enzyme of the present invention and a composition containing the same can be prepared. For example, preparation is possible by the method described below.

The transformant having introduced thereinto the object gene is mass-cultured in a liquid medium. After the mass culture, a predetermined inducer may be administered to the transformant to induce the expression of the object gene. For example, in the case where the vector uses Lac operon, IPTG can be administered to induce the expression of the object gene.

After the mass expression, the culture supernatant or a disruption liquid obtained by disrupting cells ultrasonically or with a cell-wall digesting enzyme, for example, is collected. In the supernatant or the disruption liquid, the enzyme of the present invention is abundantly present. The supernatant or the disruption liquid may be directly used as an enzyme-containing liquid composition, or it is also possible that the liquid composition is subjected to a purification treatment and collected as a purified enzyme.

The purification treatment can be performed, for example, by salting-out, membrane separation, or column chromatography. Such an operation can be performed alone, and it is also possible to combine a plurality of operations. The kind of column chromatography is not limited, and it is possible to use a column containing an antibody or the like that specifically acts on the enzyme, or it is also possible to use a column capable of interacting with tag domains previously added to the enzyme, such as His tags.

By such a method, the enzyme consisting of an amino acid sequence set forth in SEQ ID NO: 1 or its homologue or the enzyme consisting of an amino acid sequence set forth in SEQ ID NO: 2 or its homologue can be mass-prepared. These enzymes can be used for the production of galacto-oligosaccharides.

<Method for Producing GOS>

According to a fourth mode of the present invention, a method for producing GOS using *Paenibacillus pabuli*-derived lactase, such as the enzyme described above, is provided.

*Paenibacillus pabuli*-derived lactase, such as the enzyme described in detail in the first mode of the present invention, has a galacto-oligosaccharide-producing activity. Therefore, use thereof makes it possible to produce GOS from lactose. The method or conditions for GOS production are not limited. An example will be given below for explanation, but the present invention is not limited thereto.

The method for producing GOS of the present invention includes a step of bringing an enzyme into contact with lactose, and a step of producing GOS as a result of the contact. The method may also include an optional step of isolating and purifying the produced GOS.

The method for producing GOS of the present invention includes bringing the enzyme described above into contact with lactose. The enzyme to come into contact with lactose may be in the state of being purified from the microorganisms that produce the enzyme (purified enzyme). Alternatively, it is possible to bring microorganisms themselves into contact with lactose, and it is also possible that a mixture also containing other factors, such as a disruption product or an extract of the microorganisms, is brought into contact with lactose. In terms of preventing a side reaction, it is preferable to bring a purified enzyme into contact with lactose.

"Purified enzyme" means an enzyme solution or an enzyme solid obtained through a predetermined purification treatment. This mainly means that enzymes other than the enzyme are substantially absent, or that other enzymes are reduced.

By mixing the enzyme and the like with a lactose-containing solution or by mixing lactose with a solution containing the enzyme and the like, a reaction system for producing galacto-oligosaccharides (a mixture containing a solvent, lactose, and the enzyme of the present invention) is formed. The solvent is arbitrary, but is usually water or an aqueous solvent containing water as a main component.

The content of lactose in the reaction system is not particularly limited and can be arbitrarily set. The content may be, for example, based on the whole reaction system amount, 1 to 80 mass %, 2 to 70 mass %, or 4 to 60 mass %.

In a certain embodiment, the content may further be 4 to 50 mass %, 4 to 40 mass %, 4 to 30 mass %, 4 to 20 mass %, or 4 to 10 mass %. In such a region where the substrate concentration is relatively low, the enzyme consisting of an amino acid sequence set forth in SEQ ID NO: 1 or its family enzyme is preferably used. This is because they are excellent in terms of Km value and also have a sufficient activity even at a low substrate concentration.

In another embodiment, the content may also be 5 to 60 mass %, 10 to 60 mass %, 20 to 60 mass %, 30 to 60 mass %, and 40 to 60 mass %. In such a region where the substrate concentration is relatively high, the enzyme consisting of an amino acid sequence set forth in SEQ ID NO: 2 or its family enzyme is preferably used. They simultaneously achieve an excellent GOS-producing activity and a trisaccharide GOS selection activity, and can mass-produce trisaccharide GOS within a short period of time.

The content of the enzyme of the present invention in the reaction system is not particularly limited and can be arbitrarily set. The content may be, for example, in the reaction system, 0.1 to 10 LU/mL or 0.1 to 10 OU/mL, for example.

The GOS-producing activity varies depending on the reaction system. The content of the enzyme of the present invention may be determined as follows.

As a first step, in a specific reaction system (the content of lactose, the content of the enzyme of the present invention, reaction pH, reaction temperature, reaction time, etc.), the GOS production relative to the content of the enzyme of the present invention is checked.

As a second step, the lactase activity (at least either of LU/mL and OU/mL) of the enzyme of the present invention contained in the reaction system is measured.

As a third step, using the lactase activity measured in the second step as an index, the amount of the enzyme of the present invention contained in the reaction system is adjusted (the content of the enzyme of the present invention is increased or reduced).

As a fourth step, it is contained such that the content of the enzyme of the present invention contained in the reaction system is the adjusted value.

The first step and the second step may be reversed.

The pH of the reaction system is not particularly limited and can be arbitrarily set. It may be, for example, 3 to 9, 4 to 8, or 5 to 7. As a matter of course, the pH may be constant or vary.

The temperature of the reaction system is not particularly limited and can be arbitrarily set. It may be, for example, 20 to 75° C., 30 to 75° C., 40 to 75° C., 50 to 70° C., or 60 to 70° C. As a matter of course, the temperature may be constant or vary. It is preferable to select a temperature at which lactose contained in the reaction system dissolves.

The reaction time is not particularly limited and can be arbitrarily set. It may be, for example, 1 to 100 hours, 12 to 60 hours, or 24 to 48 hours.

The series of production processes may be batch-wise or continuous. In a batch-wise method, a predetermined amount of enzyme and raw material lactose are fed into the reactor, GOS is produced for a predetermined period of time, and then a GOS-containing mixture is collected from the reactor. In a continuous method, the enzyme and/or raw material lactose is continuously or intermittently fed into the reactor. Then, while producing GOS, a GOS-containing mixture is collected from the reactor.

In the present invention, the state of the lactose to serve as a raw material is not particularly limited. It is possible to use a lactose solution obtained by dissolution in an arbitrary solvent. In addition, it is also possible that a lactose-containing mixture, such as whey (a supernatant resulting from curdling), a concentrate thereof, or a skim milk powder, is used as the lactose raw material.

At the time of completion of the above steps, monosaccharides, disaccharides, and GOS are all present in the reaction system. The mixture may be directly used as a GOS solution, or it is also possible to purify GOS therefrom. The technique for purifying GOS is not particularly limited, and an arbitrary technique can be adopted. For example, separation into fractions can be performed by column chromatography using a cation exchange resin with activated carbon or metal ion coordinated thereto or a resin for gel filtration.

Conditions in the column chromatography, such as the column size, the kind of solvent, and the flow rate of the solvent, can also be arbitrarily adjusted.

Present Invention 2

Hereinafter, the present invention 2 will be described.

In the present invention, "oligosaccharide" means a polysaccharide compound, ranging from trisaccharides to decasaccharides.

In the present invention, a galacto-oligosaccharide (also expressed as GOS) mainly means an oligosaccharide represented by the following general formula.

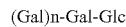

(Gal)n-Gal-Glc

Here, Gal represents a galactose residue, Glc represents a glucose residue, and n is an integer of 1 to 8, especially an integer of 1 to 3. The linkage pattern of each intersaccharide linkage is not particularly limited, but is typically a β-1,4-glycoside linkage.

Lactase is an enzyme that can hydrolyze lactose into β-galactose and glucose. Upon the decomposition, the β-galactosyl group can be transferred to another molecule. Transfer into water generates β-galactose, while transfer into lactose (Gal-Glc) generates a trisaccharide galacto-oligosaccharide (Gal-Gal-Glc) (n in the above formula is 1).

When such a transfer reaction of the β-galactosyl group takes place with a trisaccharide galacto-oligosaccharide (Gal-Gal-Glc) (n in the above formula is 1), a tetrasaccharide galacto-oligosaccharide ((Gal)2-Gal-Glc) (n in the above formula is 2) is generated. Similarly, when the reaction takes place with a tetrasaccharide galacto-oligosaccharide (n in the above formula is 2), a pentasaccharide galacto-oligosaccharide (n in the above formula is 3) is generated.

In the method for producing a galacto-oligosaccharide of the present invention, bacteria of the genus *Paenibacillus* are used as lactase-producing microorganisms. It has not been reported in the past that bacteria of the genus *Paenibacillus* generally produce galacto-oligosaccharides.

As bacteria of the genus *Paenibacillus*, for example, the following bacteria can be mentioned. All of the following bacteria can be isolated from soil, for example, or have been deposited to public institutions, and thus are readily accessible to those skilled in the art.

*Paenibacillus thermophilus* (e.g., Deposit No. DSM 24746)
*Paenibacillus popilliae* (e.g., Deposit No. DSM 22700)
*Paenibacillus thiaminolyticus* (e.g., Deposit No. NBRC 15656)
*Paenibacillus pabuli* (e.g., Deposit No. NBRC 13638)
*Paenibacillus alvei* (e.g., Deposit No. NBRC 3343)
*Paenibacillus alginolyticus* (e.g., Deposit No. NBRC 15375)
*Paenibacillus chibensis* (e.g., Deposit No. NBRC 15958)
*Paenibacillus chitinolyticus* (e.g., Deposit No. NBRC 15660)
*Paenibacillus chondroitinus* (e.g., Deposit No. NBRC 15376)
*Paenibacillus glucanolyticus* (e.g., Deposit No. NBRC 15330)
*Paenibacillus lautus* (e.g., Deposit No. NBRC 15380)
*Paenibacillus macerans* (e.g., Deposit No. NBRC 15307)
*Paenibacillus peoriae* (e.g., Deposit No. NBRC 15541)
*Paenibacillus polymyxa* (e.g., Deposit No. NBRC 15309 and Deposit No. JCM 2507)
*Paenibacillus validus* (e.g., Deposit No. NBRC 15382)
*Paenibacillus apiarius* (e.g., Deposit No. DSM 5581)
*Paenibacillus jamilae* (e.g., Deposit No. DSM 13815)
*Paenibacillus kribbensis* (e.g., Deposit No. JCM 11465)
*Paenibacillus terrae* (e.g., Deposit No. JCM 11466)

It has turned out that the bacteria of the genus *Paenibacillus* described above are capable of producing galacto-oligosaccharides from lactose as a raw material. Generally, the presence of a lactase activity does not necessarily lead to the production of galacto-oligosaccharides. Because the galacto-oligosaccharide productivity cannot be confirmed from the gene sequence, in order to confirm the galacto-oligosaccharide productivity, it is necessary to perform actual tests to confirm the galacto-oligosaccharide productivity. In many bacteria of the genus *Paenibacillus* described above, galacto-oligosaccharide productivity has been confirmed. In addition, as reasons why microorganisms produce oligosaccharides, the following causes are possible: a saccharide is changed into an oligosaccharide, whereby the saccharide is unlikely to be utilized by different kinds of microorganisms; oligosaccharides are accumulated as storage substances in a nutrient-rich state, and the oligosaccharides are utilized in a nutrient-poor state; and osmotic changes accompanying lactose decomposition is prevented/reduced. Microorganisms of neighboring species have similar genes and thus can implement similar survival strategies. Therefore, presumably, microorganisms of neighboring species have the similar capacity to produce oligosaccharides. From the above, it has been surmised that galacto-oligosaccharides are produced by whole microorganisms belonging to the genus *Paenibacillus*. In addition, it is also possible to use a mutant strain of these bacteria of the genus *Paenibacillus*, a recombinant produced by genetic engineering, or the like.

Generally, the growth rate of bacteria of the genus *Paenibacillus* is high. In addition, they have antibacterial properties against various microorganisms. Therefore, in the production of galacto-oligosaccharides, the mass culture of these bacteria is easier as compared with yeast and the like.

Meanwhile, unlike bacteria of the genus *Bacillus*, no bacteria of the genus *Paenibacillus* pathogenic to human health are known. Thus, presumably, they also have high operational safety.

FIG. 4 is a phylogenetic tree, analyzing these bacteria of the genus *Paenibacillus* and the genus *Bacillus*. As can be seen from FIG. 4, the genus *Paenibacillus* is a genus clearly branched from the genus *Bacillus*.

In the method for producing a galacto-oligosaccharide of the present invention, cells of bacteria of the genus *Paenibacillus* and/or a galacto-oligosaccharide-producing enzyme of the bacteria is brought into contact with lactose to produce a galacto-oligosaccharide. As the galacto-oligosaccharide-producing enzyme, a purified enzyme may be used. In addition, it is also possible to use a mixture containing the enzyme (enzyme-containing mixture). As the enzyme-containing mixture, a treated product of cells, such as a disruption product or an extract of cells, can be mentioned. The treated product may be solid or liquid. In the case where the bacteria secrete the enzyme outside the cells, the medium from which cells have been removed can also be used as an enzyme-containing mixture.

More specifically, in a typical embodiment of the method for producing a galacto-oligosaccharide of the present invention, the following steps are implemented:

an optional step of culturing bacteria of the genus *Paenibacillus* (culture step),
a step of bringing cells of bacteria of the genus *Paenibacillus* and/or a galacto-oligosaccharide-producing enzyme thereof into contact with raw material lactose (mixing step),
a step of producing galacto-oligosaccharides from the raw material lactose to obtain a galacto-oligosaccharide mixture (galacto-oligosaccharide production step), and
an optional step of purifying galacto-oligosaccharides from the GOS mixture (galacto-oligosaccharide purification step).

The series of production processes may be batch-wise or continuous. In a batch-wise method, a predetermined amount of bacteria of the genus *Paenibacillus* and raw material lactose are fed into the reactor, GOS is produced for a predetermined period of time, and then a GOS-containing mixture is collected from the reactor. In a continuous method, bacteria of the genus *Paenibacillus*, an enzyme thereof, and/or raw material lactose is continuously or intermittently fed into the reactor. Then, while producing GOS, a GOS-containing mixture is collected from the reactor.

In the present invention, the state of the lactose to serve as a raw material is not particularly limited. It is possible to use a lactose solution obtained by dissolution in an arbitrary solvent. In addition, it is also possible that a lactose-containing mixture, such as whey (a supernatant resulting from curdling), a concentrate thereof, or a skim milk powder, is used as the lactose raw material.

When making contact, for the convenience of the operation, it is preferable that lactose or bacteria of the genus *Paenibacillus* and/or a galacto-oligosaccharide-producing enzyme thereof is fluidized with a suitable solvent. The solvent is arbitrary, but is typically water or an aqueous solvent containing water as a main component.

Usually, bacteria of the genus *Paenibacillus* are cultured before being brought into contact with lactose. The culture conditions for bacteria of the genus *Paenibacillus* are not limited in any way and are arbitrary. For example, culture may be performed in a liquid medium at about 30° C. for about 3 days under anaerobic or aerobic conditions. The kind of liquid medium is not limited in any way, and arbitrary ones can be used. For example, a soybean-casein digest (SCD) medium, a brain heart infusion (BHI) medium, and the like can be mentioned.

The bacteria of the genus *Paenibacillus* obtained by culture may be alive or dead, and the cultured product or its treated product can also be advantageously used. The cultured product may also be concentrated. When the liquid medium and cells are centrifuged and washed with physiological saline, distilled water, or water, wet cells can be obtained. In addition, as treated products of the cultured product, an ultrasonic-treated product, a lytic enzyme-treated product, a surfactant-treated product, a mechanical grinding-treated product, and the like can be mentioned. Such a product is suspended in a suitable solvent, whereby a fluid containing cells and/or an enzyme of bacteria of the genus *Paenibacillus* can be obtained.

As a result of mixing lactose and bacteria of the genus *Paenibacillus*, a reaction system for producing galacto-oligosaccharides (a mixture containing a solvent, lactose, and cells and/or an enzyme of bacteria of the genus *Paenibacillus*) is formed.

The content of cells of bacteria of the genus *Paenibacillus* in the reaction system is not particularly limited and may be suitably set. The content may be, for example, as wet cells, 10 to 200 g/L, 30 to 150 g/L, and 50 to 100 g/L. In the case where an enzyme is added using an enzyme-containing mixture such as a disruption product, an extract, or a medium, the content thereof may be adjusted to such an amount that the original strain is within the above range.

The content of lactose in the reaction system is not particularly limited and may be suitably set. The content may be, for example, based on the whole reaction system amount, 5 to 60 mass % or 30 to 60 mass %. With the consumption of lactose, additional lactose may be suitably supplied.

The ratio of the content of bacteria of the genus *Paenibacillus* to the content of lactose in the reaction system (kg/kg) is not particularly limited and may be suitably set. The ratio may be, for example, as wet cells relative to the amount of lactose, 1/30 to 1/1, 1/20 to 1/2, or 1/10 to 1/5. In the case where an enzyme is added using an enzyme-containing mixture such as a disruption product, an extract, or a medium, the content thereof may be adjusted to such an amount that the original strain is within the above range.

The temperature of the reaction system is not particularly limited and can be suitably set. It may be, for example, 10 to 75° C., 20 to 60° C., or 30 to 50° C. As a matter of course, the temperature may be constant or vary.

The pH of the reaction system is not particularly limited and can be suitably set. It may be, for example, 3 to 9, 5 to 8, 6 to 8, 6 to 7.5, or 6 to 7. As a matter of course, the pH may be constant or vary.

The reaction time in the reaction system is not particularly limited and may be suitably set. It may be, for example, 1 to 50 hours, 5 to 30 hours, or 12 to 24 hours.

In order to efficiently produce galacto-oligosaccharides, the reaction system may contain an inorganic salt or the like. The content of the inorganic salt or the like is, for example, based on the whole reaction system amount, 0.00001 to 10 mass % or 0.0001 to 1 mass %. As a solvent containing an inorganic salt, a liquid medium, such as a SCD medium or a BHI medium, may be used.

At the time of completion of the above steps, monosaccharides, disaccharides, and GOS are all present in the reaction system. The mixture may be directly used as a cell-containing GOS solution or may also be used as a GOS solution after removing cells, and it is also possible to purify GOS therefrom. The method for removing cells from the cell-containing GOS solution is arbitrary. For example, centrifugation, filtering, sterilization by heating, and the like can be mentioned. The technique for purifying GOS is not particularly limited, and an arbitrary technique can be adopted. Separation into fractions can be performed by column chromatography using a cation exchange resin with activated carbon or metal ion coordinated thereto or a resin for gel filtration.

Conditions in the column chromatography, such as the column size, the kind of solvent, and the flow rate of the solvent, can also be arbitrarily adjusted.

EXAMPLES

Present Invention 1

Hereinafter, the present invention 1 will be described in detail with reference to examples. However, the present invention is not limited only to these examples.

Examples 1 and 2: Enzymes Consisting of Amino Acid Sequences Set Forth in SEQ ID NO: 1 and SEQ ID NO: 2

A genomic DNA was collected from *Paenibacillus pabuli*, and, using the same as the template, DNAs (structural genes) encoding enzymes consisting of amino acid sequences set forth in SEQ ID NO: 1 and SEQ ID NO: 2, respectively, were amplified by PCR.

The pair of primers used to amplify the structural gene encoding the enzyme consisting of an amino acid sequence set forth in SEQ ID NO: 1 (i.e., DNA consisting of a base sequence set forth in SEQ ID NO: 5) was primers 1 and 2.

```
Primer 1:
5'-GAACACAAGGTCATGAAAGCAGCAAAGGCAGAT-3'

Primer 2:
5'-CATCCTGTTAAGCTTTTACAATGCCCGAATGAC-3'
```

The pair of primers used to amplify the structural gene encoding the enzyme consisting of an amino acid sequence set forth in SEQ ID NO: 2 (i.e., DNA consisting of a base sequence set forth in SEQ ID NO: 6) was primers 3 and 4.

```
Primer 3:
5'-GAACACAAGGTCATGACCATTTTTCAATTTCCG-3'

Primer 4:
5'-CATCCTGTTAAGCTTTTAACGGATTTCCAGCCAATTG-3'
```

Each amplified structural gene was inserted into a plasmid pBIC by homologous recombination using the BIC System (TaKaRa). Each plasmid was introduced into *Brevibacillus chosinensis* to mass-express the enzyme.

After the production of each enzyme, the transformant was ultrasonically disrupted to give a cell disruption liquid. The SDS-PAGE results of the disruption liquids are shown in FIG. 1. FIG. 1A shows the SDS-PAGE results of the enzyme having an amino acid sequence set forth in SEQ ID NO: 1, and FIG. 1B shows the results of the enzyme consisting of an amino acid sequence set forth in SEQ ID NO: 2. The prepared cell disruption liquids were each ultra-filtered as necessary to concentrate the enzyme. The concentrated disruption liquid of the enzyme consisting of an amino acid sequence set forth in SEQ ID NO: 1 was defined as Example 1, and the concentrated disruption liquid of the enzyme consisting of an amino acid sequence set forth in SEQ ID NO: 2 was defined as Example 2.

As the lactase activity of Example 1, the lactose-decomposing activity was 0.4 LU/mL, and the ONPG-decomposing activity was 11.7 OU/mL. As the lactase activity of Example 2, the lactose-decomposing activity was 51.7 LU/mL, and the ONPG-decomposing activity was 240 OU/mL.

(Validation 1: Analysis of Reaction Rate Parameter)

The reaction rate parameter when using the ONPG of the enzyme of Example 1 as the substrate was determined by the following method. The specific activity (μmol/mg protein/min) upon reaction at a substrate concentration of 0.075 to 7.5 mM at 40° C. for 10 minutes was calculated, and the specific activity was plotted to each substrate concentration. At this time, 100 mM sodium phosphate (pH 6.5) was used as the buffer. From the substrate saturation curve measured by the above method, following the Michaelis-Menten equation, $K_m$ (Michaelis-Menten constant), which indicates the affinity between the enzyme and the substrate, and V (maximum velocity), which indicates how many micromoles of substrate is catalyzed in 1 minute per mg of the enzyme, were calculated. Table 1 shows a comparison thereof with the performance of β-galII. β-galII is an enzyme obtained by purifying only low-molecular lactase from a culture solution of *Bacillus circulans*, and is a main enzyme of BIOLACTA (manufactured by Amano Enzyme, Inc.) (Non-Patent Literature 1).

TABLE 1

|  | Km(mM) | Vmax (units/mg protein) |
| --- | --- | --- |
| Example 1 | 0.36 | 55.0 |
| β-gal II | 10.0* | 56.0* |

*Cited from Non-Patent Literature 1

As is clear from Table 1, although the enzyme of Example 1 has a maximum velocity comparable to that of the enzyme contained in BIOLACTA, its $K_m$, which indicates the affinity to the substrate ONPG, is significantly low. Therefore, presumably, use of the enzyme of the present invention makes it possible to efficiently produce GOS even at a lower substrate concentration than BIOLACTA.

Comparative Example

As a comparative example, an enzyme consisting of an amino acid sequence set forth in SEQ ID NO: 4 (*Bacillus circulans*-derived lactase BgaD-D) was used. In order to acquire the present enzyme, a genomic DNA was collected from the *Bacillus* sp. ATCC 31382 strain (previously named *Bacillus circulans*), and, using the same as the template, a structural gene encoding the enzyme consisting of an amino acid sequence set forth in SEQ ID NO: 4 was amplified by PCR. A start codon and a stop codon were added to the N-terminal side and the C-terminal side of the gene, respectively, and introduced into *Brevibacillus chosinensis* to mass-express the enzyme. After the production of the enzyme, the transformant was ultrasonically disrupted to give a cell disruption liquid.

(Validation 2: Analysis of GOS Production Capacity)

The GOS production capacity of each of the samples of Example 1, Example 2, and the comparative example was evaluated. In the enzyme of Example 1, lactose was blended with a 0.1 M potassium phosphate buffer (pH 6.5) containing 1 mM magnesium sulfate and 0.064 mM EDTA to a final concentration of 30 mass % based on the whole system amount, and the enzyme was added to give an activity of 1.5 LU/mL. In each of the enzyme of Example 2 and the enzyme of the comparative example, lactose was blended with a 0.1 M sodium phosphate buffer (pH 6.5) to a final concentration of 60 mass % based on the whole system amount, and the enzyme was added to give an activity of 5.0 LU/mL.

A GOS production reaction was allowed to take place for 24 hours at a reaction temperature of 30° C. for the enzyme of Example 1 and 50° C. for the enzymes of Example 2 and the comparative example. After the elapse of a predetermined period of time, a 20 wt % sulfosalicylic acid solution was added in an amount of 1/20 the reaction solution to stop the reaction.

Each of the samples of Examples 1 and 2 and the comparative example was subjected to HPLC to analyze the amount of GOS produced. The analysis was performed using, as the column, CARBOSep CHO-620 6.50×300 mm manufactured by Transgenomic under the following conditions: mobile phase: water, flow rate: 0.4 mL/min, temperature: 85° C., detection: RI. The HPLC results of each sample are shown in Table 2.

"GOS" in Table 2 means the GOS content ratio. More specifically, it is the percentage of the HPLC area of GOS relative to the total HPLC area of GOS (pentasaccharides, tetrasaccharides, trisaccharides), disaccharides (unreacted lactose and transferred disaccharides), and monosaccharides (glucose, galactose).

"Yield" means the efficiency of GOS production. More specifically, it is the percentage of GOS production/lactose consumption (GOS production and lactose consumption are calculated from HPLC).

Incidentally, hexa- or higher saccharides were not observed in Examples 1 and 2 and the comparative example.

TABLE 2

|  | Penta-saccharide (%) | Tetra-saccharide (%) | Tri-saccharide (%) | Di-saccharide (%) | Glucose + galactose (%) | GOS (%) | Yield (%) | Trisaccharide GOS production selectivity (%) |
| --- | --- | --- | --- | --- | --- | --- | --- | --- |
| Example 1 | 0.8 | 6.1 | 21.6 | 41.5 | 30.1 | 28.5 | 48.7 | 75.8 |
| Example 2 | 0.4 | 7.0 | 33.7 | 36.4 | 22.5 | 41.1 | 64.6 | 82.0 |
| Comparative Example | 6.0 | 11.0 | 23.0 | 38.5 | 21.4 | 40.0 | 65.0 | 57.5 |

As is clear from Table 2, the enzymes of Examples 1 and 2 have higher selectivity for trisaccharide GOS than the enzyme of the comparative example. It was revealed that the enzyme of the present invention has an excellent function in this respect.

In particular, the enzyme of Example 2 has a GOS yield comparable to that of the enzyme of the comparative example, and thus can simultaneously achieve a high GOS production yield and trisaccharide selectivity.

(Validation 3: Saccharide Configuration of GOS)

In GOS in human milk, due to the difference in linkage pattern, three kinds of structures, that is, 4'-GL (Galβ1-4Galβ1-4Glc), 3'-GL (Galβ1-3Galβ1-4Glc), and 6'-GL (Galβ1-6Galβ1-4Glc), are present. It is known that in most of commercially available lactase for GOS production, 4'-GL and 6'-GL are mainly produced. Meanwhile, most of bifidobacteria constantly develop a transporter to incorporate 3'-GL into the cells (Non-Patent Literature 2). That is, the advantage of 3'-GL-containing GOS is that bifidobacteria can easily grow.

Based on this, GOS by BgaD-D of the comparative example and GOS by lactase of Example 2 were analyzed by HPAEC-PAD (Thermo Fisher Scientific; ICS-3000+, Dionex CarboPac PA1 column) (FIG. 2). Incidentally, the conditions for the saccharide composition analysis are as follows.

Analysis Conditions: In HPAEC-PAD (high performance anion exchange chromatography-pulsed amperometric detection), an ion chromatograph ICS-3000 (manufactured by Thermo Scientific) was used as the device, and CarboPac PA1 (φ4 mm×250 mm, manufactured by Thermo Scientific) was used as the column. A 100 mM sodium hydroxide solution (A), a 100 mM sodium hydroxide-containing 600 mM sodium acetate solution (B), water (C), and a 50 mM sodium acetate solution (D) were used as the mobile phase, and saccharides were separated by gradient. The conditions are shown in Table 3. The reaction liquid was prepared to have a saccharide concentration of 0.5 mg/mL, thereby giving a sample for analysis. The sample was analyzed at a flow rate of 1.0 mL/min, an injection volume of 25 μL, and a column temperature of 20° C. using a detector PAD.

TABLE 3

| Time(min) | % A | % B | % C | % D |
|---|---|---|---|---|
| 0.0 | 10 | 0 | 85 | 5 |
| 25.0 | 40 | 0 | 10 | 50 |
| 60.0 | 75 | 25 | 0 | 0 |
| 60.1 | 0 | 100 | 0 | 0 |
| 65.0 | 0 | 100 | 0 | 0 |
| 65.1 | 10 | 0 | 85 | 5 |
| 72.0 | 10 | 0 | 85 | 5 |

As a result, it turned out that unlike the GOS produced by the lactase of the comparative example where 4'-GL is the main saccharide, the main GOS produced by the lactase of Example 2 is, from its peak position, highly likely to be 3'-GL (Table 4). In addition, of the GOS produced by the lactase of Example 2, trisaccharides were separated and subjected to structural analysis. As a result, the $^1$H-NMR spectrum and the $^{13}$C-NMR spectrum were consistent with the patterns of 3'-GL (Non-Patent Literature 3). From this, the main GOS produced by the present enzyme was presumed to be 3'-GL.

TABLE 4

|  | 6'-GL 19.3 min | 4'-GL 28.1 min | 3'-GL 29.8 min |
|---|---|---|---|
| Comparative Example | 2.78 | 9.14 | N.D. |
| Example 2 | 2.65 | N.D. | 16.6 |

(1)

Next, a presence confirmation test for tetrasaccharides ([Galβ1-4(Galβ1-4Galβ1-6)Glc]), which are highly allergenic and commonly referred to as 4P-X, was performed relative to the GOS produced by the lactase of the comparative example and the GOS produced by the enzyme of Example 2. Specifically, of GOS produced by these enzymes, tetrasaccharides were separated by gel filtration chromatography using Bio-Gel P2 Gel (Bio-Rad) and analyzed using HPAEC-PAD. At this time, a comparison was made with our synthesized specimen rich in 4P-X (Non-Patent Literature 4). As a result, only in the GOS produced by the enzyme of Example 2, no peak was observed in the position of 4P-X (FIG. 3). From this, it turned out that the GOS produced by the enzyme of Example 2 contained no 4P-X.

Present Invention 2

Hereinafter, the present invention 2 will be described in detail with reference to examples. However, the present invention is not limited only to these examples.
(Screening of Microorganisms with GOS Transfer Capacity)

Arbitrary soil was added to a SCD medium containing 1% lactose, and cultured with shaking at 30° C. and 250 spm for 7 days. 0.1 ml of this culture solution was transplanted to 10 mL of a medium of the same composition, and cultured with shaking at 30° C. and 250 spm for 7 days. Next, the culture solution was applied to an agar medium of the same composition, and cultured at 30° C. for about 5 days.

In addition, arbitrary soil was applied to a SCD agar medium containing 0.1% lactose, and similarly cultured at 30° C. for about 7 days.

Each obtained colony was inoculated with a platinum loop into 0.5 mL of a SCD medium containing 2% lactose placed in a 48-well plate, and cultured with shaking at 30° C. and 500 rpm (amplitude: 2 mm) for 4 days, thereby collecting a culture solution of each strain.

With respect to the culture solution of each strain, a lactose solution obtained by dissolution using a 0.2 M acetic acid buffer (pH 6.0) was added to a final lactose concentration of 25 to 30 mass %, followed by a transfer reaction at 30° C. and 500 rpm for 24 hours.

After the completion of the reaction, the reaction solution was centrifuged to collect the supernatant, and suitably diluted with pure water to give a sample for analysis. The GOS amount of each sample was measured by the HPLC analysis method (column: CARBOSep CHO-620 6.5φ×300 mm manufactured by Transgenomic, mobile phase: water, flow rate: 0.5 mL/min, temperature: 85° C., detection: RI). The presence of GOS in a sample means that the strain of the sample has GOS transfer capacity. In this manner, strains having GOS transfer capacity were selected.

The strains thus obtained included *Paenibacillus popilliae*, *Paenibacillus thermophilus*, *Paenibacillus pabuli*, *Paenibacillus alvei*, and *Paenibacillus thiaminolyticus*. That is, it was suggested that bacteria belonging to the genus *Paenibacillus* have the capacity to produce GOS from lactose.

Using a SCD medium containing 2% lactose and a BHI medium containing 2% lactose placed in a 240×200 mm test tube, the strains were each inoculated with a platinum loop into 10 mL of each medium and cultured with shaking at 30° C. and 250 spm for 4 days. As a control, bacteria belonging to the genus *Bacillus* (Deposit No. ATCC 31382 strain: previously named *Bacillus circulans*) were cultured under the same conditions.

After the completion of the culture, 0.5 ml of the culture solution was moved to a 48-well plate. 0.5 mL of a lactose solution obtained by dissolving lactose in a 0.2 M acetic acid buffer (pH 6.0) to a lactose concentration of 30 mass % was added thereto, followed by a transfer reaction at 30° C. and 500 rpm for 24 hours.

After the completion of the reaction, the contents of GOS and lactose in the reaction liquid were measured by HPLC to analyze the peak area of each component, and the GOS production capacity of each strain was evaluated. The results are shown in Table 5.

TABLE 5

| strain | Homology Search (BLAST) | | GOS Productivity | | | |
| --- | --- | --- | --- | --- | --- | --- |
| | | | SCD Medium | | BHI Medium | |
| | Homology Rate (%) | Corresponding Strain | GOS (%) | Yield (%) | GOS (%) | Yield (%) |
| P. popilliae L3185 | 100 | Sh-14 | 28.2 | 64.8 | 28.5 | 61.3 |
| P. thermophilus G1986 | 99.7 | JCA-1904 | 17.7 | 61.7 | 19.1 | 61.8 |
| P. thermophilus L3450 | 99.6 | JCA-1904 | 22.4 | 71.8 | 20.2 | 73.5 |
| P. pabuli U5889 | 99.7 | SW12 | 23.5 | 68.9 | 25.2 | 68.9 |
| P. pabuli S5390 | 99.6 | SW12 | 22.1 | 67.4 | 18.6 | 64.8 |
| P. alvei T5623 | 99.7 | N184 | 26.4 | 71.2 | 22.1 | 72.5 |
| P. thiaminolyticus N3839 | 99.6 | NBRC 15656 | 29.6 | 66.4 | 28.6 | 65.6 |
| Bacillus sp. ATCC 31382 | — | — | 17.5 | 55.2 | 18.0 | 60.6 |

"GOS" in Table 5 means the GOS content ratio. More specifically, it is the percentage of the HPLC area of GOS relative to the total HPLC area of GOS (tri- or higher saccharides, mainly pentasaccharides, tetrasaccharides, and trisaccharides), lactose, glucose, and galactose.

"Yield" in Table 5 means the efficiency of GOS production. More specifically, it is the percentage of GOS production/lactose consumption (GOS production and lactose consumption are calculated from HPLC).

The homology rate in the column "Homology Search (BLAST)" in Table 5 means the homology to the species having the highest homology (corresponding strain) in the BLAST search for the 16S rDNA base sequence of each strain utilizing the site of DNA Data Bank of Japan, etc. In the case where a homology of 99.5% or more was exhibited, such a species was identified.

Using the strains and the corresponding strains, the type strains of the identified species, the genus *Paenibacillus* having GOS transfer capacity, and the typical genus *Bacillus* in Table 5, and specifying *Aneurinibacillus aneurinilyticus* DSM 5562 as an outgroup, the 16S rDNA base sequences thereof were aligned utilizing the site of DNA Data Bank of Japan, etc., to form a phylogenetic tree. For the formation of the phylogenetic tree, a genetic information processing software GENETYX (manufactured by GENETYX Corporation) was used. FIG. 4 shows a simple molecular phylogenetic tree based on the 16S rDNA partial base sequences of the genus *Paenibacillus* and the genus *Bacillus*.

As can be seen from Table 5, it turned out that these bacteria of the genus *Paenibacillus* can produce GOS with high production proportions and yields. In addition, it turned out that these bacteria of the genus *Paenibacillus* can produce GOS with higher efficiency than the control bacteria of the genus *Bacillus*.

From this finding, other bacteria of the genus *Paenibacillus* were also evaluated for the GOS production capacity under the same conditions. Table 6 shows the used strains and the results.

TABLE 6

| Genus Paenibacillus | | GOS Productivity | | | |
| --- | --- | --- | --- | --- | --- |
| | | SCD Medium | | BHI Medium | |
| | | GOS | (yield %) | GOS | (yield %) |
| P. alginolyticus | NBRC 15375$^T$ | ++ | | + | |
| P. alvei | NBRC 3343$^T$ | + | | ++ | |
| P. chibensis | NBRC 15958$^T$ | ++ | | ++ | |
| P. chitinolyticus | NBRC 15660$^T$ | − | | + | |
| P. chondroitinus | NBRC 15376$^T$ | ++ | | ++ | |

TABLE 6-continued

| Genus Paenibacillus | | GOS Productivity | | | |
| --- | --- | --- | --- | --- | --- |
| | | SCD Medium | | BHI Medium | |
| | | GOS | (yield %) | GOS | (yield %) |
| P. glucanolyticus | NBRC 15330$^T$ | − | | + | |
| P. lautus | NBRC 15380$^T$ | − | | + | |
| P. macerans | NBRC 15307$^T$ | − | | ++ | |
| P. pabuli | NBRC 13638$^T$ | + | | + | |
| P. peoriae | NBRC 15541$^T$ | + | | ++ | |
| P. polymyxa | NBRC 15309$^T$ | ++ | | ++ | |
| P. thiaminolyticus | NBRC 15656$^T$ | + | | 13.6 | (64.1) |
| P. validus | NBRC 15382$^T$ | − | | + | |
| P. apiarius | DSM 5581$^T$ | + | | ++ | |
| P. jamilae | DSM 13815$^T$ | + | | ++ | |
| P. polymyxa | JCM 2507$^T$ | ++ | | 10.7 | (61.6) |
| P. kribbensis | JCM 11465$^T$ | 16.6 | (60.2) | 14.0 | (60.4) |
| P. terrae | JCM 11466$^T$ | + | | ++ | |
| Bacillus sp. | ATCC 31382 | 7.5 | (57.0) | 11.0 | (60.6) |

The value in the column "GOS" in Table 6 means the GOS production proportion; "++" means that the GOS production proportion was 1% or more, "+" means that the GOS production proportion was less than 1%, and "−" means no implementation. "Yield" in Table 6 has the same meaning as in Table 5.

As is clear from the results of Table 6, it turned out that bacteria of the genus *Paenibacillus* had the capacity to produce GOS. In addition, although there was no great difference in the GOS production capacity of *Bacillus circulans* between two kinds of media, in the case of bacteria of the genus *Paenibacillus*, it turned out that a great difference may occur in GOS production capacity between two kinds of media. This result suggests that the GOS production capacity of bacteria of the genus *Paenibacillus* is greatly influenced by changes in the conditions, such as the medium. From this, it was suggested that by setting the optimal conditions for each kind of bacteria of the genus *Paenibacillus*, GOS production and/or a GOS yield more excellent than before may be obtained. It is non-trivial and surprising that the genus *Paenibacillus* is usable for GOS production, and the yield can be higher than conventional.

The invention claimed is:

1. An enzyme composition comprising lactose and a purified enzyme having an amino acid sequence selected from the group consisting of:
   (a) the amino acid sequence set forth in SEQ ID NO: 1, wherein the enzyme has galacto-oligosaccharide producing activity;
   (b) the amino acid sequence set forth in SEQ ID NO: 2, wherein the enzyme has galacto-oligosaccharide producing activity;
   (e) an amino acid sequence having at least 90% sequence identity to the amino acid sequence set forth in SEQ ID NO: 1, wherein the enzyme has galacto-oligosaccharide producing activity; and
   (f) an amino acid sequence having at least 96% sequence identity to the amino acid sequence set forth in SEQ ID NO: 2, wherein the enzyme has galacto-oligosaccharide producing activity;
   wherein the galacto-oligosaccharide producing activity has about 75% by mass or more trisaccharide galacto-oligosaccharide selectivity, and
   wherein the purified enzyme has a lactase activity comprising 0.2 LU/mL (1 μmol of glucose in 1 minute per milliliter) or more under pH 6.5 and 40° C.; or 0.5 OU/mL (1 μmol of o-nitrophenyl in 1 minute per mL) or more under pH 6.5 and 40° C.; or both.

2. A method for producing a galacto-oligosaccharide, comprising:
   contacting lactose with the enzyme according to claim 1.

3. The enzyme composition of claim 1, wherein the enzyme is purified from *Paenibacillus*.

4. The enzyme composition of claim 1, wherein the enzyme is purified from *Paenibacillus pabuli*.

5. The enzyme composition of claim 1, wherein the galacto-oligosaccharide producing activity has about 45 to about 70 mass % yield of galacto-oligosaccharides.

6. A purified enzyme having an amino acid sequence selected from the group consisting of:
   (a) an amino acid sequence having at least 90% sequence identity to the amino acid sequence set forth in SEQ ID NO: 1, with at least one substitution modification of the amino acid sequence set forth in SEQ ID NO:1, and wherein the enzyme has galacto-oligosaccharide producing activity; and
   (b) an amino acid sequence having at least 96% sequence identity to the amino acid sequence set forth in SEQ ID NO: 2, with at least one substitution modification of the amino acid sequence set forth in SEQ ID NO:2, and wherein the enzyme has galacto-oligosaccharide producing activity;
   wherein the galacto-oligosaccharide producing activity has about 75% by mass or more trisaccharide galacto-oligosaccharide selectivity, and
   wherein the purified enzyme has a lactase activity comprising 0.2 LU/mL (1 μmol of glucose in 1 minute per milliliter) or more measured by adding the purified enzyme to a lactose solution and quantitatively determining glucose production under pH 6.5 and 40° C. conditions; or the purified enzyme has a lactase activity comprising 0.5 OU/mL (1 μmol of o-nitrophenyl in 1 minute per mL) or more measured by adding the purified enzyme to an o-nitrophenyl-β-galactopyranoside solution and quantitatively determining o-nitrophenyl production under pH 6.5 and 40° C. conditions; or both.

* * * * *

SEQUENCE LISTING

<160> NUMBER OF SEQ ID NOS: 6

<210> SEQ ID NO 1
<211> LENGTH: 1016
<212> TYPE: PRT
<213> ORGANISM: Paenibacillus pabuli

<400> SEQUENCE: 1

```
Met Lys Ala Ala Lys Ala Asp Leu Lys Trp Leu Gly Asp Val Ser
1               5                   10                  15

Val Phe Glu Val Asn Arg Leu Lys Ala Tyr Ser Asp His Arg Tyr
                20                  25                  30

Tyr Arg Thr Met Glu Glu Ala Leu Lys Ser Asp Glu Met Asp Met
                35                  40                  45

Arg Tyr Ser Leu Asn Gly Met Trp Lys Phe Asn Tyr Ala Val Arg
                50                  55                  60

Pro Asp Cys Arg Pro Glu His Phe Tyr Ala Ala Asp Phe Ser Ser
                65                  70                  75

Asp Gly Trp Asp Asp Ile Glu Val Pro Gly His Ile Gln Leu Gln
                80                  85                  90

Gly Tyr Gly Gln Ile Gln Tyr Val Asn Thr Gln Tyr Pro Trp Asp
                95                  100                 105

Gly Leu Asn Glu Leu Arg Pro Pro Ala Leu Pro Glu Asp Asn Asn
                110                 115                 120

Ala Val Gly Ser Tyr Ile Arg Thr Phe His Leu Pro Ala Gly Trp
                125                 130                 135

Gly Asn Ser Pro Val Tyr Ile Ser Phe Gln Gly Val Glu Ser Ala
                140                 145                 150

Phe Tyr Val Trp Leu Asn Gly His Phe Val Gly Tyr Gly Glu Asp
                155                 160                 165

Ser Phe Thr Pro Ser Asp Phe Asp Leu Thr Pro Phe Leu Gln Glu
                170                 175                 180

Gly Glu Asn Lys Leu Ala Val Glu Val Tyr Gln Arg Ser Thr Gly
                185                 190                 195

Ser Trp Leu Glu Asp Gln Asp Phe Trp Arg Phe Ser Gly Ile Phe
                200                 205                 210

Arg Glu Val Tyr Leu Tyr Thr Val Pro Ala Ala His Ile Arg Asp
                215                 220                 225

Val Arg Val Arg Thr Asp Leu Asp Ala Ser Tyr Ser Gln Gly Thr
                230                 235                 240

Leu Gln Leu Asp Leu Lys Leu Glu Gly Ala Ala Ala Gly Ala
                245                 250                 255

Arg Val Glu Ala Glu Leu Arg Asp Ala Gln Gly Asn Val Val Gln
                260                 265                 270

Thr Phe Gly Val Asn Val Gln Asp Gly Gln Ala Ser Val Arg Lys
                275                 280                 285

Glu Val Gly Glu Val Asn Leu Trp Ser Ala Glu Ile Pro Tyr Leu
                290                 295                 300

Tyr Arg Leu Tyr Leu Arg Val Tyr Asp Ser Ala Gly Glu Leu Val
                305                 310                 315

Glu Val Val Pro Gln Ala Val Gly Phe Arg Val Phe Glu Met Ile
                320                 325                 330

Asp Lys Val Met His Ile Asn Gly Lys Arg Ile Val Phe Lys Gly
                335                 340                 345
```

```
Val Asn Arg His Glu Phe Asn Pro His Arg Gly Arg Ala Ile Thr
                350                 355                 360

Lys Glu Asp Met Leu Trp Asp Ile Arg Thr Ile Lys Gln Asn Asn
                365                 370                 375

Met Asn Ala Val Arg Thr Ser His Tyr Pro Asn Gln Ser Leu Trp
                380                 385                 390

Tyr Glu Leu Cys Asp Glu Tyr Gly Val Tyr Val Ile Asp Glu Met
                395                 400                 405

Asn Leu Glu Thr His Gly Ser Trp Gln Lys Leu Gly Ala Val Glu
                410                 415                 420

Pro Ser Trp Val Ile Pro Gly Asp Arg Pro Glu Trp Leu Asp Ile
                425                 430                 435

Val Met Asp Arg Ala Val Ser Met Val Glu Arg Asp Lys Asn His
                440                 445                 450

Pro Ser Ile Leu Ile Trp Ser Cys Gly Asn Glu Ser His Gly Gly
                455                 460                 465

Glu Val Ile Phe Lys Val Ser Glu Tyr Phe Arg Thr Tyr Asp Pro
                470                 475                 480

Thr Arg Leu Val His Tyr Glu Gly Val Phe His Asp Arg Arg Phe
                485                 490                 495

Asn Asp Thr Ser Asp Met Glu Ser Arg Met Tyr Ala Lys Pro Ala
                500                 505                 510

Asp Ile Glu Ala Tyr Leu Asn Asp Asn Pro Glu Lys Pro Tyr Ile
                515                 520                 525

Ser Cys Glu Tyr Met His Ala Met Gly Asn Ser Ile Gly Gly Met
                530                 535                 540

His Lys Tyr Thr Glu Leu Glu Asp Lys Tyr Pro Met Tyr Gln Gly
                545                 550                 555

Gly Phe Ile Trp Asp Tyr Ile Asp Gln Ala Ile Tyr Lys Lys Asp
                560                 565                 570

Arg Tyr Gly Lys Pro Phe Leu Ala Tyr Gly Gly Asp Phe Gly Asp
                575                 580                 585

Arg Pro Ser Asp Tyr Ser Phe Cys Gly Asp Gly Ile Val Tyr Ala
                590                 595                 600

Asn Arg Gln Val Thr Ala Lys Met Gln Glu Val Lys Phe Leu Tyr
                605                 610                 615

Gln Asn Ile Lys Leu Phe Pro Asp Arg Gly Gly Val Arg Ile Val
                620                 625                 630

Asn Gly Asn Leu Phe Ala Asn Thr Ser Gln Tyr Ala Leu Thr Tyr
                635                 640                 645

Ser Leu Glu Arg Glu Gly Val Thr Val Leu Ser Gly Thr Leu Glu
                650                 655                 660

Ala Ala Val Ala Pro Gly Glu Glu Ala Phe Val Glu Leu Pro Leu
                665                 670                 675

Ala Thr Glu Gln Leu Ala Pro Gly Glu Tyr Ala Val Asn Ala Ala
                680                 685                 690

Phe Val Leu Arg Glu Ser Thr Leu Trp Ala Glu Lys Gly Asp Glu
                695                 700                 705

Val Ala Phe Gly Gln Phe Val Phe Thr Gln Glu Ala Ala Glu Gly
                710                 715                 720

Ala Ser Val Thr Thr Asp Leu Asn Gln Val Asn Ala Ile Gln Val
                725                 730                 735

Val Glu Gly Asp Val Asn Ile Gly Val Arg Ala Gly Ser Thr His
```

```
                          740                 745                 750
Val Leu Phe Ser Lys Ala Phe Gly Thr Leu Val Ser Leu Lys Phe
                  755                 760                 765

Ser Gly Gln Glu Thr Ile Ala Gln Met Pro Ala Pro Leu Phe Trp
                  770                 775                 780

Arg Ala Thr Thr Asp Asn Asp Lys Gly Thr Ser Met Gly Phe Glu
                  785                 790                 795

Leu Gly Ala Trp Tyr Ala Ala Ser Leu Leu Pro Lys Cys Ile Glu
                  800                 805                 810

Trp Lys Ala Glu Gln Gln Gly Glu Tyr Arg Ile Glu Phe Thr
                  815                 820                 825

Tyr Lys Leu Asn Ile Ser Thr Glu Val Lys Ala Lys Val Ala Tyr
                  830                 835                 840

Thr Val Arg Ala Asp Gly Ser Val Leu Val Gln Asn Thr Tyr Gln
                  845                 850                 855

Gly Thr Ala Gly Leu Pro Asp Leu Pro Ile His Ala Leu Ser Phe
                  860                 865                 870

Lys Thr Ser Pro Glu Phe Asp Arg Val Gln Trp Leu Ala Leu Gly
                  875                 880                 885

Pro Glu Glu Asn Tyr Ala Asp Arg Ala Phe Gly Ala Arg Leu Gly
                  890                 895                 900

Ile His Glu Ser Ser Val Ala Asp Thr Val Ala Pro Tyr Leu Val
                  905                 910                 915

Pro Gln Glu Ser Gly Asn Arg Thr Gly Val Arg Trp Ala Lys Leu
                  920                 925                 930

Thr Asp Ala Ala Gly Arg Gly Phe Arg Ile Glu Ala Ala Ser Ala
                  935                 940                 945

Pro Ile Glu Leu Asn Val Ser Pro Tyr Thr Ala Phe Glu Leu Glu
                  950                 955                 960

Asn Ala Gln His Ala Tyr Glu Leu Pro Pro Val His Tyr Thr Val
                  965                 970                 975

Val Thr Val Ala Gly Lys Gln Met Gly Val Gly Gly Asp Asp Ser
                  980                 985                 990

Trp Gly Ala Pro Val His Pro Glu Tyr Arg Ile Pro Ser Asp Gly
                  995                1000                1005

Glu Leu Gln Phe Glu Phe Val Ile Arg Ala Leu
                 1010                1015

<210> SEQ ID NO 2
<211> LENGTH: 447
<212> TYPE: PRT
<213> ORGANISM: Paenibacillus pabuli

<400> SEQUENCE: 2

Met Thr Ile Phe Gln Phe Pro Lys Asp Phe Arg Trp Gly Thr Ala
1               5                  10                  15

Thr Ala Ser Tyr Gln Val Glu Gly Ala Ala Gln Glu Gly Gly Arg
                  20                  25                  30

Gly Val Ser Ile Trp Asp Thr Phe Ala Arg Thr Pro Gly Lys Val
                  35                  40                  45

Phe Asn Gly Asp Asn Gly Asp Ile Ala Cys Asp Gly Tyr His Arg
                  50                  55                  60

Tyr Glu Glu Asp Ile Glu Leu Met Lys Lys Leu Gly Ile Asn Thr
                  65                  70                  75
```

-continued

```
Tyr Arg Phe Ser Ile Ala Trp Pro Arg Ile Pro Asp Gly Asp
             80                  85                  90

Gly Glu Ile Asn Arg Glu Gly Leu Asp Phe Tyr His Arg Phe Val
         95                 100                 105

Asp Lys Leu Leu Glu Ala Gly Ile Glu Pro Phe Cys Thr Leu Tyr
             110                 115                 120

His Trp Asp Leu Pro Gln Val Leu Glu Asp Ile Gly Gly Trp Gly
             125                 130                 135

Asn Arg Arg Thr Val Asp Ala Phe Val Lys Tyr Ala Glu Val Ile
             140                 145                 150

Phe Lys Glu Phe Ser Gly Lys Ile Asn Phe Trp Leu Thr Phe Asn
             155                 160                 165

Glu Pro Trp Cys Ile Ala Phe Leu Ser Asn Leu Leu Gly Val His
             170                 175                 180

Ala Pro Gly Asn Lys Asp Leu Gln Thr Ser Leu Asn Val Ala His
             185                 190                 195

Gly Leu Leu Val Ala His Gly Lys Ala Val Gln Ser Phe Arg Arg
             200                 205                 210

Leu Gly Thr Thr Gly Lys Ile Gly Ile Ala Pro Asn Val Cys Trp
             215                 220                 225

Ala Glu Pro Tyr Ser Lys Thr Pro Glu Asp Gln Ala Ala Cys Asp
             230                 235                 240

Arg Ser Ile Ala Leu Asn Thr Asp Trp Phe Leu Asp Pro Ile Tyr
             245                 250                 255

Lys Gly Ser Tyr Pro Gln Phe Met Val Asp Trp Phe Glu Gln Ala
             260                 265                 270

Gly Ala Thr Val Pro Ile Gln Asp Gly Asp Met Glu Ile Ile Ser
             275                 280                 285

Gln Pro Ile Asp Leu Leu Gly Ile Asn Tyr Tyr Thr Met Gly Ile
             290                 295                 300

Asn Arg Tyr Asn Pro Glu Ala Gly Val Leu Gln Ser Glu Glu Leu
             305                 310                 315

Asn Met Gly Leu Thr Arg Thr Asp Ile Gly Trp Pro Ile Glu Ser
             320                 325                 330

Arg Gly Leu Tyr Glu Phe Met His Tyr Leu Gln Lys Tyr Gly Asn
             335                 340                 345

Val Glu Val Tyr Ile Thr Glu Asn Gly Ala Cys Ile Asn Asp Gln
             350                 355                 360

Pro Glu Asn Gly Ile Val Asn Asp Glu Arg Arg Ile Ser Tyr Tyr
             365                 370                 375

Glu Gln His Leu Ala Gln Ile His Arg Ile Ile Ser Asp Gly Ile
             380                 385                 390

Asn Leu Lys Gly Tyr Met Ala Trp Ser Leu Met Asp Asn Phe Glu
             395                 400                 405

Trp Ala Glu Gly Tyr Arg Met Arg Phe Gly Leu Ile His Val Asp
             410                 415                 420

Tyr Arg Thr Leu Lys Arg Thr Pro Lys Glu Ser Tyr Tyr Trp Tyr
             425                 430                 435

Gln Asn Val Ile Lys Asn Trp Leu Glu Ile Arg
             440                 445
```

<210> SEQ ID NO 3
<211> LENGTH: 1737
<212> TYPE: PRT

<213> ORGANISM: Bacillus circulans

<400> SEQUENCE: 3

```
Val Lys Lys Ala Ile Ser Cys Val Phe Leu Ile Ser Ala Leu Ile
 1               5                  10                  15

Leu Ser Ser Phe Gln Val Pro Val Gln Gly Gln Ala Met Ser Lys
                20                  25                  30

Thr Thr Ser Ala Ala Gly Asn Ser Val Ser Tyr Asp Gly Glu Arg
                35                  40                  45

Arg Val Asn Phe Asn Glu Asn Trp Arg Phe Gln Arg Glu Thr Asn
                50                  55                  60

Gly Ser Ile Ala Gly Ala Gln Asn Pro Gly Phe Asp Asp Ser Ser
                65                  70                  75

Trp Arg Lys Leu Asn Leu Pro His Asp Trp Ser Ile Glu Leu Asp
                80                  85                  90

Phe Asn Lys Asn Ser Leu Ala Thr His Glu Gly Gly Tyr Leu Asp
                95                 100                 105

Gly Gly Ile Gly Trp Tyr Arg Lys Thr Phe Thr Ile Pro Glu Ser
               110                 115                 120

Met Lys Gly Lys Arg Ile Ser Leu Asp Phe Asp Gly Val Tyr Met
               125                 130                 135

Asn Ser Thr Thr Tyr Leu Asn Gly Glu Val Leu Gly Thr Tyr Pro
               140                 145                 150

Phe Gly Tyr Asn Ala Phe Ser Tyr Asp Ile Ser Asp Lys Leu Tyr
               155                 160                 165

Lys Asp Gly Arg Ala Asn Val Leu Val Lys Val Asn Asn Thr
               170                 175                 180

Gln Pro Ser Ser Arg Trp Tyr Ser Gly Ser Gly Ile Tyr Arg Asn
               185                 190                 195

Val Tyr Leu Thr Val Thr Asp Pro Ile His Val Ala Arg Tyr Gly
               200                 205                 210

Thr Phe Val Thr Thr Pro Asn Leu Glu Lys Ser Ile Lys Glu Asp
               215                 220                 225

Arg Ala Asp Val Asn Ile Lys Thr Lys Ile Ser Asn Asp Ala Ala
               230                 235                 240

Glu Ala Lys Gln Val Lys Ile Lys Ser Thr Ile Tyr Asp Gly Ala
               245                 250                 255

Gly Asn Thr Val Gln Thr Val Glu Thr Glu Lys Thr Ala Ala
               260                 265                 270

Ala Gly Thr Val Thr Pro Phe Glu Gln Asn Thr Val Ile Lys Gln
               275                 280                 285

Pro Lys Leu Trp Ser Ile Asp Lys Pro Tyr Arg Tyr Asn Leu Val
               290                 295                 300

Thr Glu Val Ile Val Gly Gly Gln Thr Val Asp Thr Tyr Glu Thr
               305                 310                 315

Lys Phe Gly Val Arg Tyr Phe Lys Phe Asp Glu Asn Glu Gly Phe
               320                 325                 330

Ser Leu Asn Gly Glu Tyr Met Lys Leu His Gly Val Ser Met His
               335                 340                 345

His Asp Leu Gly Ala Leu Gly Ala Ala Thr Asn Ala Arg Gly Val
               350                 355                 360

Glu Arg Gln Met Gln Ile Met Lys Asp Met Gly Val Asn Ala Ile
               365                 370                 375
```

```
Arg Val Thr His Asn Pro Ala Ser Pro Glu Leu Leu Glu Ala Ala
            380                 385                 390
Asn Lys Leu Gly Leu Phe Ile Ile Glu Glu Ala Phe Asp Ser Trp
            395                 400                 405
Ala Gln Ser Lys Lys Pro Tyr Asp Tyr Gly Arg Phe Phe Asn Ala
            410                 415                 420
Trp Ala Glu His Asp Ile Lys Glu Met Val Asp Arg Gly Lys Asn
            425                 430                 435
Glu Pro Ala Ile Ile Met Trp Ser Ile Gly Asn Glu Ile Tyr Asp
            440                 445                 450
Thr Thr Asn Ala Ala Gly Val Glu Thr Ala Arg Asn Leu Val Gly
            455                 460                 465
Trp Val Lys Glu Ile Asp Thr Thr Arg Pro Thr Thr Ile Gly Glu
            470                 475                 480
Asp Lys Thr Arg Gly Asp Lys Val Asn Val Thr Pro Ile Asn Ser
            485                 490                 495
Tyr Ile Lys Glu Ile Phe Asn Ile Val Asp Val Val Gly Leu Asn
            500                 505                 510
Tyr Ser Glu Asn Asn Tyr Asp Gly Tyr His Lys Gln Asn Pro Ser
            515                 520                 525
Trp Lys Leu Tyr Gly Ser Glu Thr Ser Ser Ala Thr Arg Ser Arg
            530                 535                 540
Gly Val Tyr Thr His Pro Tyr Gln Tyr Asn Gln Ser Thr Lys Tyr
            545                 550                 555
Ala Asp Leu Gln Gln Ser Ser Tyr Asp Asn Asp Tyr Val Gly Trp
            560                 565                 570
Gly Arg Thr Ala Glu Asp Ala Trp Lys Tyr Asp Arg Asp Leu Lys
            575                 580                 585
His Ile Ala Gly Gln Phe Ile Trp Thr Gly Phe Asp Tyr Ile Gly
            590                 595                 600
Glu Pro Thr Pro Tyr Tyr Asn Ser Tyr Pro Ala Lys Ser Ser Tyr
            605                 610                 615
Phe Gly Ala Val Asp Thr Ala Gly Phe Pro Lys Asp Ile Phe Tyr
            620                 625                 630
Tyr Tyr Gln Ser Gln Trp Lys Lys Glu Pro Met Val His Leu Leu
            635                 640                 645
Pro His Trp Asn Trp Lys Glu Gly Glu Lys Val Arg Val Leu Ala
            650                 655                 660
Tyr Thr Asn Ala Ser Lys Val Glu Leu Val Leu Asn Gly Glu Ser
            665                 670                 675
Leu Gly Glu Lys Asn Tyr Asp Asn Lys Gln Thr Ser Trp Gly Ala
            680                 685                 690
Pro Tyr Lys Glu Thr Lys Asp Gly Lys Thr Tyr Leu Glu Trp Ala
            695                 700                 705
Val Pro Phe Lys Pro Gly Lys Leu Glu Ala Val Ala Lys Asp Glu
            710                 715                 720
Asn Gly Lys Val Ile Ala Arg Asp Gln Val Val Thr Ala Gly Glu
            725                 730                 735
Pro Ala Ser Val Arg Leu Thr Ala Asp Arg Lys Val Val Lys Ala
            740                 745                 750
Asp Gly Thr Asp Leu Ser Phe Ile Thr Ala Asp Ile Val Asp Ser
            755                 760                 765
Lys Gly Ile Val Val Pro Asp Ala Asp His Leu Ile Thr Phe Asn
```

```
                        770             775             780
Val Thr Gly Gln Gly Glu Leu Ala Gly Val Asp Asn Gly Asn Ala
                785             790             795
Ser Ser Val Glu Arg Tyr Lys Asp Asn Lys Arg Lys Ala Phe Ser
                800             805             810
Gly Lys Ala Leu Ala Ile Val Gln Ser Ser Lys Leu Ser Gly Lys
                815             820             825
Ile Thr Val His Ala Ser Val Ala Gly Leu Ser Ser Asp Ser Thr
                830             835             840
Ser Val Phe Thr Val Thr Pro Ala Asp His Asp Lys Lys Ile Val
                845             850             855
Ala Gly Ile Asp Asp Val Asn Leu Thr Val Asp Val Asn Glu Ala
                860             865             870
Pro Lys Leu Pro Ser Glu Ile Lys Val Tyr Tyr Ser Asp Glu Ser
                875             880             885
Ala Ala Ala Lys Asn Val Thr Trp Asp Glu Val Asp Pro Lys Gln
                890             895             900
Tyr Ser Thr Val Gly Glu Phe Thr Val Glu Gly Ser Val Glu Gly
                905             910             915
Thr Ser Leu Lys Ala Lys Ala Phe Val Val Lys Gly Ile Val
                920             925             930
Ala Val Lys Pro Tyr Ser Thr Ala Thr Lys Val Gly Val Gln Pro
                935             940             945
Val Leu Pro Glu Lys Ala Thr Leu Leu Tyr Ser Asp Gly Thr Thr
                950             955             960
Lys Gly Ala Thr Val Thr Trp Asp Glu Ile Pro Glu Asp Lys Leu
                965             970             975
Ala Lys Glu Gly Arg Phe Thr Val Glu Gly Ser Val Glu Gly Thr
                980             985             990
Asp Leu Lys Ala Asn Val Tyr Val Arg Val Thr Asn Glu Val Lys
                995             1000            1005
Ser Val Asn Ile Met Leu Gln Glu Gln Gly Ser Ala Tyr Pro Lys
                1010            1015            1020
Leu Glu Ala Thr Phe Thr Asn Pro Ala Asp Asn Leu Gln His Leu
                1025            1030            1035
Asn Asp Gly Ile Lys Ser Tyr Thr Asn Pro Val Asn Arg Trp
                1040            1045            1050
Thr Asn Trp Thr Arg Thr Pro Arg Asp Ala Gly Asp Ser Ile Thr
                1055            1060            1065
Val Asn Phe Gly Lys Lys His Val Ile Asn Asn Leu Asp Leu Phe
                1070            1075            1080
Val Phe Thr Asp Ser Gly Thr Val Val Pro Glu Lys Ala Glu Val
                1085            1090            1095
Gln Tyr Trp Asp Gly Thr Ala Trp Lys Asp Val Glu Asn Leu Thr
                1100            1105            1110
Gln Pro Ser Pro Tyr Val Val Glu Lys Asn Glu Leu Thr Phe Asp
                1115            1120            1125
Ala Val Ala Thr Glu Lys Leu Lys Phe His Leu Thr Pro Ser Val
                1130            1135            1140
Lys Gly Lys Phe Leu Ala Leu Thr Glu Ala Glu Val Tyr Ala Asp
                1145            1150            1155
Gln Ile Val Met Gly Glu Thr Ala Lys Leu Gln Ser Ile Thr Val
                1160            1165            1170
```

```
Asn Gly Lys Ala Leu Glu Gly Phe Asp His Ala Lys Asn Tyr
            1175                1180                1185

Glu Leu Val Leu Pro Tyr Gly Ser Glu Leu Pro Lys Ile Glu Ala
            1190                1195                1200

Ala Ala Ala Asp Asn Ala Thr Val Thr Ile Leu Pro Ala Phe Ser
            1205                1210                1215

Tyr Pro Gly Thr Ala Lys Leu Phe Val Thr Ser Glu Asp Gly Lys
            1220                1225                1230

Val Thr Thr Glu Tyr Ser Ile Gly Val Ser Thr Glu Pro Lys
            1235                1240                1245

Leu Val Ser Ala Glu Leu Ser Ala Asp Lys Thr Asn Val Met Glu
            1250                1255                1260

Asp Asp Ile Ile Asp Leu Lys Val Ile Gly Leu Phe Glu Ser Lys
            1265                1270                1275

Glu Lys Ile Asp Val Thr Asp Ser Gln Pro Thr Tyr Glu Phe Asp
            1280                1285                1290

Gln Gln Ile Ile Lys Ile Glu Gly Asn Lys Leu Tyr Ala Leu Glu
            1295                1300                1305

Thr Gly Asn Val Lys Val Lys Val Thr Val Thr Tyr Lys Gly Val
            1310                1315                1320

Ser Val Thr Thr Pro Ala Leu Glu Phe Thr Ile Ala Lys Asn Pro
            1325                1330                1335

Ala Pro Lys Tyr Ile Thr Ser Leu Glu Pro Val Thr Val Val
            1340                1345                1350

Lys Lys Gly Glu Ala Pro Glu Leu Pro Ala Thr Val Val Ala His
            1355                1360                1365

Tyr Asn Arg Gly Ile Pro Arg Asp Val Lys Val Lys Trp Glu Arg
            1370                1375                1380

Ile Asn Pro Ser Lys Tyr Gln Gln Leu Gly Glu Phe Thr Val Ser
            1385                1390                1395

Gly Met Val Glu Gly Thr Asp Ile Lys Ala Gln Ala Lys Val Ile
            1400                1405                1410

Val Lys Gly Ala Val Ala Val Glu Asp Ile Arg Met Ala Val Leu
            1415                1420                1425

Leu Lys Gln Met Pro Gln Leu Pro Gly Lys Val Thr Val Tyr Tyr
            1430                1435                1440

Ser Asp Gly Ala Glu Glu Gln Arg Ala Val Lys Trp Glu Glu Ile
            1445                1450                1455

Pro Gln Glu Glu Leu Glu Asn Val Gly Glu Phe Lys Val Lys Gly
            1460                1465                1470

Asp Val Asn Gly Val Lys Leu Lys Ala Thr Ala Thr Ile Arg Val
            1475                1480                1485

Thr Asp Glu Val Gly Gly Glu Gln Asn Ile Ser Arg Ala Lys Asn
            1490                1495                1500

Gly Tyr Glu Tyr Pro Lys Ala Glu Ala Ser Phe Thr Asn Asn Gly
            1505                1510                1515

Pro Gly Ser Ser Asp Arg Ile Glu Ala Ile Asn Asp Asp Val Ile
            1520                1525                1530

Ser Tyr Glu Ala Asn Pro His Asn Arg Trp Thr Asn Trp Gln Pro
            1535                1540                1545

Val Pro Arg Ala Gly Asp Trp Val Ser Ile Thr Phe Gly Asp Tyr
            1550                1555                1560
```

-continued

Glu Pro Thr Glu Tyr Asp Val Asp Ser Met Glu Ile His Trp Phe
              1565                1570                1575

Ala Asp His Gly Thr Ser Tyr Pro Glu Arg Phe Gln Ile Glu Tyr
        1580                1585                1590

Lys Ser Gly Asp Ser Trp Lys Glu Val Thr Ser Leu Lys Ser Asp
        1595                1600                1605

Pro Ala Ser Pro Ala Leu Gly Lys Ala Asn Val Tyr Ser Phe Asp
        1610                1615                1620

Arg Val Lys Thr Ser Ala Ile Arg Val Lys Met Thr Ala Gln Ala
        1625                1630                1635

Gly Lys Ser Leu Ala Ile Thr Glu Leu Lys Val Phe Ser Lys Trp
        1640                1645                1650

Pro Lys Ala Gly Thr Glu Pro Glu Val Thr Asp Ile Lys Val Gly
        1655                1660                1665

Gly Lys Ser Ile Leu Glu Asp Phe Glu Gln Lys Gly Asp His Tyr
        1670                1675                1680

Glu Val Thr Ile Asp Ala Gly Asp Ala Asn Val Met Pro Lys Ile
        1685                1690                1695

Asn Val Lys Ala Lys Asp Gln Thr Ser Ile Thr Ile Val Pro Ala
        1700                1705                1710

Val Thr Ser Pro Ser Thr Ala Lys Val Ile Ala Lys Ser Glu Asp
        1715                1720                1725

Gly Lys Lys Val Lys Val Tyr Ser Ile His Tyr Lys
        1730                1735

<210> SEQ ID NO 4
<211> LENGTH: 812
<212> TYPE: PRT
<213> ORGANISM: Bacillus circulans

<400> SEQUENCE: 4

Gly Asn Ser Val Ser Tyr Asp Gly Glu Arg Arg Val Asn Phe Asn
1               5                   10                  15

Glu Asn Trp Arg Phe Gln Arg Glu Thr Asn Gly Ser Ile Ala Gly
            20                  25                  30

Ala Gln Asn Pro Gly Phe Asp Asp Ser Ser Trp Arg Lys Leu Asn
        35                  40                  45

Leu Pro His Asp Trp Ser Ile Glu Leu Asp Phe Asn Lys Asn Ser
        50                  55                  60

Leu Ala Thr His Glu Gly Gly Tyr Leu Asp Gly Ile Gly Trp
        65                  70                  75

Tyr Arg Lys Thr Phe Thr Ile Pro Glu Ser Met Lys Gly Lys Arg
        80                  85                  90

Ile Ser Leu Asp Phe Asp Gly Val Tyr Met Asn Ser Thr Thr Tyr
        95                  100                 105

Leu Asn Gly Glu Val Leu Gly Thr Tyr Pro Phe Gly Tyr Asn Ala
        110                 115                 120

Phe Ser Tyr Asp Ile Ser Asp Lys Leu Tyr Lys Asp Gly Arg Ala
        125                 130                 135

Asn Val Leu Val Val Lys Val Asn Asn Thr Gln Pro Ser Ser Arg
        140                 145                 150

Trp Tyr Ser Gly Ser Gly Ile Tyr Arg Asn Val Tyr Leu Thr Val
        155                 160                 165

Thr Asp Pro Ile His Val Ala Arg Tyr Gly Thr Phe Val Thr Thr
        170                 175                 180

```
Pro Asn Leu Glu Lys Ser Ile Lys Glu Asp Arg Ala Asp Val Asn
                185                 190                 195

Ile Lys Thr Lys Ile Ser Asn Asp Ala Ala Glu Ala Lys Gln Val
                200                 205                 210

Lys Ile Lys Ser Thr Ile Tyr Asp Gly Ala Gly Asn Thr Val Gln
                215                 220                 225

Thr Val Glu Thr Glu Glu Lys Thr Ala Ala Gly Thr Val Thr
                230                 235                 240

Pro Phe Glu Gln Asn Thr Val Ile Lys Gln Pro Lys Leu Trp Ser
                245                 250                 255

Ile Asp Lys Pro Tyr Arg Tyr Asn Leu Val Thr Glu Val Ile Val
                260                 265                 270

Gly Gly Gln Thr Val Asp Thr Tyr Glu Thr Lys Phe Gly Val Arg
                275                 280                 285

Tyr Phe Lys Phe Asp Glu Asn Glu Gly Phe Ser Leu Asn Gly Glu
                290                 295                 300

Tyr Met Lys Leu His Gly Val Ser Met His His Asp Leu Gly Ala
                305                 310                 315

Leu Gly Ala Ala Thr Asn Ala Arg Gly Val Glu Arg Gln Met Gln
                320                 325                 330

Ile Met Lys Asp Met Gly Val Asn Ala Ile Arg Val Thr His Asn
                335                 340                 345

Pro Ala Ser Pro Glu Leu Leu Glu Ala Ala Asn Lys Leu Gly Leu
                350                 355                 360

Phe Ile Ile Glu Glu Ala Phe Asp Ser Trp Ala Gln Ser Lys Lys
                365                 370                 375

Pro Tyr Asp Tyr Gly Arg Phe Phe Asn Ala Trp Ala Glu His Asp
                380                 385                 390

Ile Lys Glu Met Val Asp Arg Gly Lys Asn Glu Pro Ala Ile Ile
                395                 400                 405

Met Trp Ser Ile Gly Asn Glu Ile Tyr Asp Thr Thr Asn Ala Ala
                410                 415                 420

Gly Val Glu Thr Ala Arg Asn Leu Val Gly Trp Val Lys Glu Ile
                425                 430                 435

Asp Thr Thr Arg Pro Thr Thr Ile Gly Glu Asp Lys Thr Arg Gly
                440                 445                 450

Asp Lys Val Asn Val Thr Pro Ile Asn Ser Tyr Ile Lys Glu Ile
                455                 460                 465

Phe Asn Ile Val Asp Val Val Gly Leu Asn Tyr Ser Glu Asn Asn
                470                 475                 480

Tyr Asp Gly Tyr His Lys Gln Asn Pro Ser Trp Lys Leu Tyr Gly
                485                 490                 495

Ser Glu Thr Ser Ser Ala Thr Arg Ser Arg Gly Val Tyr Thr His
                500                 505                 510

Pro Tyr Gln Tyr Asn Gln Ser Thr Lys Tyr Ala Asp Leu Gln Gln
                515                 520                 525

Ser Ser Tyr Asp Asn Asp Tyr Val Gly Trp Gly Arg Thr Ala Glu
                530                 535                 540

Asp Ala Trp Lys Tyr Asp Arg Asp Leu Lys His Ile Ala Gly Gln
                545                 550                 555

Phe Ile Trp Thr Gly Phe Asp Tyr Ile Gly Glu Pro Thr Pro Tyr
                560                 565                 570
```

```
Tyr Asn Ser Tyr Pro Ala Lys Ser Tyr Phe Gly Ala Val Asp
            575                 580                 585

Thr Ala Gly Phe Pro Lys Asp Ile Phe Tyr Tyr Gln Ser Gln
            590                 595                 600

Trp Lys Lys Glu Pro Met Val His Leu Leu Pro His Trp Asn Trp
            605                 610                 615

Lys Glu Gly Glu Lys Val Arg Val Leu Ala Tyr Thr Asn Ala Ser
            620                 625                 630

Lys Val Glu Leu Val Leu Asn Gly Glu Ser Leu Gly Glu Lys Asn
            635                 640                 645

Tyr Asp Asn Lys Gln Thr Ser Trp Gly Ala Pro Tyr Lys Glu Thr
            650                 655                 660

Lys Asp Gly Lys Thr Tyr Leu Glu Trp Ala Val Pro Phe Lys Pro
            665                 670                 675

Gly Lys Leu Glu Ala Val Ala Lys Asp Glu Asn Gly Lys Val Ile
            680                 685                 690

Ala Arg Asp Gln Val Val Thr Ala Gly Glu Pro Ala Ser Val Arg
            695                 700                 705

Leu Thr Ala Asp Arg Lys Val Val Lys Ala Asp Gly Thr Asp Leu
            710                 715                 720

Ser Phe Ile Thr Ala Asp Ile Val Asp Ser Lys Gly Ile Val Val
            725                 730                 735

Pro Asp Ala Asp His Leu Ile Thr Phe Asn Val Thr Gly Gln Gly
            740                 745                 750

Glu Leu Ala Gly Val Asp Asn Gly Asn Ala Ser Ser Val Glu Arg
            755                 760                 765

Tyr Lys Asp Asn Lys Arg Lys Ala Phe Ser Gly Lys Ala Leu Ala
            770                 775                 780

Ile Val Gln Ser Ser Lys Leu Ser Gly Lys Ile Thr Val His Ala
            785                 790                 795

Ser Val Ala Gly Leu Ser Ser Asp Ser Thr Ser Val Phe Thr Val
            800                 805                 810

Thr Pro

<210> SEQ ID NO 5
<211> LENGTH: 3051
<212> TYPE: DNA
<213> ORGANISM: Paenibacillus pabuli

<400> SEQUENCE: 5 atg aaa gca gca aag gca gat ttg aaa tgg ctc ggg gat gta agc      45 gta ttc gag gta aac cgt ttg aag gct tat tcg gac cat cga tat      90 tat cga aca atg gaa gag gca ttg aag tcg gat gaa atg gac atg     135 cgc tac agc ctg aac ggc atg tgg aag ttc aac tac gcg gtt cga     180 ccg gat tgc cgc ccg gag cat ttc tat gca gcc gat ttc tcc agc     225 gat gga tgg gat gac att gaa gta ccc gga cat atc cag ctg caa     270 ggc tac ggc caa att caa tac gtg aac acc caa tac cca tgg gac     315 ggc ttg aat gaa ttg cgt cca ccg gct cta ccg gaa gac aac aat     360 gcg gtg ggc agc tac atc cgg acg ttc cac ctg ccg gca ggt tgg     405 gga aac agc cct gta tat att tcg ttc caa ggc gtg gag tcg gcc     450 ttt tac gtt tgg tta aat ggc cac ttc gtc ggt tac ggc gaa gat     495
```

-continued

| | |
|---|---|
| agt ttt acg cca tcc gat ttt gac ctg acg cca ttc ctc caa gag | 540 |
| ggt gag aac aaa ctg gcc gtc gaa gtg tac cag cgg agt acg gga | 585 |
| agc tgg ctg gaa gat cag gat ttc tgg cgt ttc tct ggc att ttc | 630 |
| cgc gaa gtg tac ctg tac acg gtt cct gct gca cat atc cgg gat | 675 |
| gtt cgc gtg cgc aca gac ctc gat gca tcc tat tcg caa ggt acg | 720 |
| ctg cag ctg gac ctg aaa ctt gag gga gca gcg gct gca ggc gct | 765 |
| cgc gtg gag gct gaa ttg cgc gac gca cag gga aat gtg gtt caa | 810 |
| acg ttt ggc gta aat gta caa gat ggc caa gct tcc gta cgc aaa | 855 |
| gaa gtc ggt gag gta aac ctg tgg agt gcg gaa att cct tac ttg | 900 |
| tat cgt tta tac ctg cgt gta tac gac tcg gcc ggg gaa ctc gtt | 945 |
| gaa gtg gtg cct caa gcc gtc ggc ttc cgc gta ttc gaa atg atc | 990 |
| gac aag gtg atg cac atc aac ggc aaa cga atc gtc ttc aaa ggc | 1035 |
| gtg aac cgt cat gag ttc aac ccg cat cgc ggc cgg gcc atc acc | 1080 |
| aag gaa gac atg ctg tgg gac att cgg acc atc aag caa aac aac | 1125 |
| atg aat gcg gtg cgt acc tcc cac tac ccg aac caa agt ttg tgg | 1170 |
| tac gag ctg tgt gat gaa tac ggc gtg tac gtg atc gac gaa atg | 1215 |
| aat ctt gaa acg cat gga tcc tgg caa aag ctc ggt gcc gtc gag | 1260 |
| cca tca tgg gtg att ccc ggc gac cgg ccg gaa tgg ttg gat atc | 1305 |
| gtc atg gat cgt gcc gta tcc atg gta gag cgg gac aaa aac cat | 1350 |
| cca tcc atc ctg atc tgg tct tgc ggc aac gaa tcc cat ggc ggc | 1395 |
| gaa gtg atc ttc aag gtt tcg gag tac ttc aga acg tat gat ccg | 1440 |
| acc cgg ctg gtc cat tac gaa ggc gtt ttc cat gac cgc cgc ttc | 1485 |
| aat gac acg agc gac atg gag tcg cgc atg tat gcc aaa cct gcg | 1530 |
| gat atc gaa gcc tat ttg aac gac aat ccg gag aag cct tat atc | 1575 |
| agc tgc gaa tac atg cat gca atg ggc aac tcg atc ggc ggc atg | 1620 |
| cac aaa tac acg gaa ctg gaa gac aag tac ccg atg tat caa ggc | 1665 |
| gga ttc atc tgg gat tac atc gat cag gcc att tac aaa aag gat | 1710 |
| cgt tac ggc aag ccg ttt ctg gcc tat ggc ggc gat ttc ggc gac | 1755 |
| cgc ccg tcg gac tat tcg ttc tgc ggg gac ggc atc gtg tat gcg | 1800 |
| aac cgt caa gtc acc gca aaa atg caa gaa gtc aag ttc ctg tac | 1845 |
| cag aac atc aaa ttg ttc ccg gac cgc ggc ggc gtg cgc atc gtc | 1890 |
| aat ggc aat ctg ttc gcg aat aca tcg caa tat gcg cta acg tac | 1935 |
| agc ctg gag cgc gaa ggc gta acc gta tta agc gga aca ttg gaa | 1980 |
| gca gcc gtt gct ccg ggc gag gaa gcg ttc gtg gag ctt ccg ctc | 2025 |
| gct acc gag cag ctt gca ccg ggc gaa tat gcc gtc aat gcg gcg | 2070 |
| ttc gtg ctt cgt gaa tcc acg ctg tgg gcg gaa aaa ggg gac gaa | 2115 |
| gtg gca ttt ggt caa ttc gtg ttt acg cag gaa gcc gct gaa ggg | 2160 |
| gcg tcg gta acc act gat ctg aat caa gtg aac gct att caa gtg | 2205 |
| gtt gaa ggc gac gtc aac atc ggg gtt cgt gcg gga agc acc cat | 2250 |

-continued

| | |
|---|---|
| gtg ttg ttc tcc aaa gcg ttc gga acg ctg gta tcg ctg aag ttc | 2295 |
| tcc ggt cag gag acg att gcc caa atg cct gca ccg ctc ttc tgg | 2340 |
| cgt gca acg acg gat aac gat aaa gga acg tcc atg ggc ttt gag | 2385 |
| ctt ggg gca tgg tat gcg gca agc ctg ctg ccg aaa tgc atc gaa | 2430 |
| tgg aaa gcc gag caa cag cag ggt gag tac cgg atc gaa ttt acg | 2475 |
| tat aag ctg aat att tcc act gaa gtt aaa gca aag gtt gct tat | 2520 |
| acg gtt cgc gcg gat ggc agc gtt ctt gta cag aac acc tat caa | 2565 |
| gga aca gcg gga ttg ccg gat ctt ccg atc cac gct ctg tca ttc | 2610 |
| aaa aca tcg cct gag ttc gac cgt gta cag tgg ctg gca ttg ggg | 2655 |
| cct gag gaa aac tat gcg gac cgt gcc ttc ggt gcc cgc cta ggc | 2700 |
| atc cac gaa agc tct gtc gcc gac acg tac gcg cct tac ctt gtg | 2745 |
| cct caa gag tcc ggc aac cgt acc ggc gta cgt tgg gcg aag ctg | 2790 |
| acg gat gcg gcc gga cgc ggt ttc cgc atc gag gcg gct tca gct | 2835 |
| cca atc gag ctg aac gtg tcg ccg tat acg gct ttt gag ctg gag | 2880 |
| aac gcg cag cat gcc tat gaa ctg ccg cca gtc cac tac acg gtt | 2925 |
| gta acg gtg gcg ggc aaa caa atg ggc gtc ggc ggc gat gac agc | 2970 |
| tgg ggc gct ccg gtg cat ccg gaa tac cgc atc ccg tcg gac ggc | 3015 |
| gag ctt caa ttc gag ttt gtc att cgg gca ttg taa | 3051 |

<210> SEQ ID NO 6
<211> LENGTH: 1344
<212> TYPE: DNA
<213> ORGANISM: Paenibacillus pabuli

<400> SEQUENCE: 6

| | |
|---|---|
| atg acc att ttt caa ttt ccg aaa gac ttt cgc tgg ggg acg gct | 45 |
| acg gct tcg tac caa gta gag gga gca gca caa gag gga gga cgc | 90 |
| ggt gta tcc atc tgg gat acg ttt gcg cgt aca ccg ggt aaa gta | 135 |
| ttc aac ggg gat aac ggg gat atc gca tgc gac ggt tac cat cgt | 180 |
| tat gaa gaa gac att gag tta atg aag aaa ctg ggc atc aat acg | 225 |
| tat cga ttc tcc atc gca tgg ccg cgc atc att ccg gac ggt gat | 270 |
| gga gag atc aac cgt gaa ggg ctg gac ttc tac cat cgg ttc gtc | 315 |
| gat aaa ttg ctt gaa gcg gga atc gaa ccg ttc tgc acc ctc tat | 360 |
| cac tgg gat ttg ccg caa gtg ctc gaa gac atc ggc ggt tgg ggc | 405 |
| aac cgc aga acg gta gat gct ttc gtg aaa tat gcg gaa gtc atc | 450 |
| ttc aaa gag ttc tcc ggc aaa atc aac ttc tgg ctg acg ttc aac | 495 |
| gag cca tgg tgc atc gcg ttc ctg tcc aat ctg ctg ggc gtg cac | 540 |
| gca ccg ggc aac aaa gac ctg caa acg tcg ctg aac gtt gcc cac | 585 |
| ggc ctg ctc gtt gcg cac ggc aaa gcc gtc caa tcg ttc cgt cgt | 630 |
| ctc ggc acg aca ggc aaa atc ggg atc gct ccg aac gta tgc tgg | 675 |
| gct gag cct tac agc aaa acg ccg gaa gac cag gct gcc tgc gat | 720 |
| cgc tcc atc gcg ctg aac acg gac tgg ttc ctt gac ccg atc tat | 765 |
| aaa ggc tcc tac ccg caa ttc atg gtg gac tgg ttc gag caa gcc | 810 |

```
ggg gcg acg gta ccg atc cag gat ggg gac atg gag atc att tcg        855 cag ccg att gac ctg ctg ggc att aat tat tac acc atg ggc atc        900 aat cgg tat aac cct gaa gca ggc gtg ctg caa tcg gaa gaa ctc        945 aac atg ggt ctg acg cgt acc gat att ggc tgg ccg atc gaa tcg        990 cgc ggc ttg tac gag ttc atg cac tat ttg caa aaa tac gga aac       1035 gtg gaa gtg tat atc acc gag aac ggt gca tgc atc aac gat cag       1080 ccc gag aat ggc atc gtc aac gac gag cgc cgc atc tcg tat tat       1125 gag cag cat ttg gcc cag att cac cgg atc atc agc gac ggg atc       1170 aac ctc aaa ggg tac atg gcg tgg tcg ctt atg gac aat ttt gag       1215 tgg gca gaa ggg tat cgc atg cgt ttc ggg ctc atc cat gtg gat       1260 tac cgc aca ttg aaa cgc acg ccc aaa gag agc tac tac tgg tac       1305 cag aac gta atc aaa aac aat tgg ctg gaa atc cgt taa               1344
```